United States Patent [19]

Van Gestel et al.

[11] Patent Number: 4,770,689

[45] Date of Patent: Sep. 13, 1988

[54] HERBICIDAL IMIDAZOLE-5-CARBOXYLIC ACID DERIVATIVES

[75] Inventors: Jozef F. E. Van Gestel, Vosselaar, Belgium; William R. Lutz, Riehen, Switzerland; Guy R. E. Van Lommen, Berlaar, Belgium; Hanspeter Fischer, Bottmingen, Switzerland; Marc F. J. Schroven, Heist Op Den Berg, Belgium; Rudolph C. Thummel, Courgenay, Switzerland

[73] Assignee: Janssen Pharmaceutica N.V., Beerse, Belgium

[21] Appl. No.: 944,694

[22] Filed: Dec. 19, 1986

Related U.S. Application Data

[63] Continuation-in-part of Ser. No. 838,067, Mar. 10, 1986, abandoned.

[51] Int. Cl.[4] .................. A01N 43/50; C07D 403/06; C07D 401/06

[52] U.S. Cl. .......................................... 71/92; 71/90; 544/296; 544/310; 544/316; 544/317; 544/319; 544/320; 544/321; 544/322; 544/324; 544/327; 544/328; 544/331; 544/333; 546/256; 546/278; 548/318; 548/321; 548/336; 548/343

[58] Field of Search ............... 548/343, 336, 318, 321; 546/256, 278; 544/296, 333, 310, 316, 317, 319, 320, 321, 322, 324, 327, 328, 331; 71/90, 92

[56] References Cited

U.S. PATENT DOCUMENTS

| | | | |
|---|---|---|---|
| 3,354,173 | 11/1967 | Godefroi et al. | 548/343 |
| 4,182,624 | 1/1980 | Soeder et al. | 71/92 |
| 4,595,400 | 6/1986 | Leone-Bay et al. | 71/92 |

Primary Examiner—Richard A. Schwartz
Attorney, Agent, or Firm—Geoffrey G. Dellenbaugh

[57] ABSTRACT

A method for controlling weeds preferably in the crops of useful plants by using a 1-methyl-1H-imidazole-5-carboxylic acid derivative; herbicidal compositions containing the same; 1-methyl-1H-imidazole-5-carboxylic acid derivatives.

25 Claims, No Drawings

HERBICIDAL IMIDAZOLE-5-CARBOXYLIC ACID DERIVATIVES

REFERENCE TO RELATED APPLICATIONS

This application is a continuation-in-part of our copending application Ser. No. 838,067, filed Mar. 10, 1986, now abandoned.

BACKGROUND OF THE INVENTION

In U.S. Pat. No. 3,354,173 there are described a number of 1-substituted-1H-imidazole-5-carboxylic esters as compounds having hypnotic properties. In U.S. Pat. No. 4,182,624 there are described a further series of 1-substituted-1H-imidazole-5-carboxylic acids as plant growth regulators.

The present invention relates to a novel method for controlling weeds, preferaby selectively in crops of useful plants, by appling a 1-methyl-1H-imidazole-5-carboxylic acid derivative. Further the invention relates to novel compounds used in the said new method, to processes for preparing these compounds and to compositions containing them as active ingredients.

DESCRIPTION OF THE INVENTION

The present invention is concerned with a method for controlling weeds, which method comprises applying to said weeds or to the locus thereof of a herbicidally effective amount of a 1-methyl-1H-imidazole-5-carboxylic acid derivative of formula

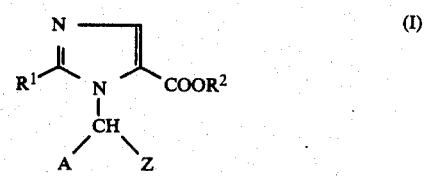

(I)

or a stereoisomeric form thereof, or a salt thereof, or a quaternised form thereof, or a N-oxide thereof, wherein
$R^1$ is hydrogen or mercapto;
$R^2$ is hydrogen, $C_1$-$C_7$alkyl, $C_3$-$C_7$alkenyl, $C_3$-$C_7$alkynyl, $C_1$-$C_7$alkyloxy$C_1$-$C_7$alkyl, aryl$C_1$-$C_5$alkyl or $C_3$-$C_7$cycloalkyl; wherein aryl is phenyl optionally substituted with one to three substituents independently selected from $C_1$-$C_5$alkyl, $C_1$-$C_5$alkyloxy and halo;
A is hydrogen; $C_3$-$C_7$cycloalkyl optionally substituted with one or two $C_1$-$C_5$alkyl radicals; $C_1$-$C_7$alkyl optionally substituted with $C_1$-$C_7$alkyloxy or with an Ar radical; or $C_1$-$C_7$alkyl substituted with both a $C_1$-$C_7$alkyloxy and an Ar radical; or a radical selected from pyridinyl, pyrimidinyl, naphthalenyl, furanyl and thienyl, each unsubstituted or substituted with one or two radicals independently selected from $C_1$-$C_5$alkyl, $C_1$-$C_5$alkyloxy, halo, nitro, amino, mono- and di$C_1$-$C_5$alkylamino, —NH—CO—G, cyano, trifluoromethyl and difluoromethoxy;
said radical Ar being phenyl, pyridinyl, pyrimidinyl, naphthalenyl, furanyl or thienyl, each unsubstituted or substituted with one or two and in case Ar is phenyl also with three substituents selected from $C_1$-$C_5$alkyl, $C_1$-$C_5$alkyloxy, halo, nitro, amino, mono- and di$C_1$-$C_5$alkylamino, —NH—CO—G, cyano, trifluoromethyl and difluoromethoxy;
Z is naphthalenyl, thienyl, furanyl, pyrimidinyl, phenyl or pyridinyl, each unsubstituted or substituted with one or two substituents and in case Z is phenyl also with three substituents independently selected from $C_1$-$C_5$alkyl, $C_1$-$C_5$alkyloxy, halo, cyano, nitro, amino, mono- and di$C_1$-$C_5$alkylamino, —NH—CO—G, trifluoromethyl and difluoromethoxy; and
G is $C_1$-$C_6$alkyl.

Some of the active ingredients of formula (I) are known from U.S. Pat. No. 3,354,173, while most of them are new.

Surprisingly, the compounds of formula (I) show strong herbicidal properties and are therefore useful to control weeds. These properties gain importance by the fact that some crops of useful plants are not damaged, or are only slightly harmed at high dosages when treated with compounds of formula (I). Consequently, the compounds of formula (I) are valuable selective herbicides in crops of useful plants, such as sugar beet, rape, soybeans, cotton, sunflower, cereals, especially wheat, barley, rye and oats, rice, both upland rice and paddy rice, and maize. Especially in rice crops a broad range of application rates can be employed, preferably if the rice crops are transplanted rice crops, and if the compounds of formula (I) are applied after transplantation. In maize crops selective herbicidal action is observed both at preemergence and at postemergence treatment.

The active ingredients (a.i.) of formula (I) are usually applied at application rates of 0.01 to 5.0 kg of active ingredient per hectare in order to achieve satisfying results. Sometimes, depending on the environmental conditions, the application rates may exceed the above designated limitations. However, the preferred application rates are between 0.05 kg and 1.0 kg a.i. per hectare.

As used in the foregoing definitions $C_1$-$C_5$alkyl denotes straight or branch chained saturated hydrocarbon radicals having from 1 to 5 carbon atoms, e.g. methyl, ethyl, n-propyl, isopropyl, the four butyl isomers and the pentyl isomers; $C_1$-$C_7$alkyl includes $C_1$-$C_5$alkyl radicals and the higher homologs thereof having 6 or 7 carbon atoms; halo is fluoro, chloro, bromo or iodo, with fluoro and chloro being preferred; $C_3$-$C_7$alkenyl defines straight and branch chained hydrocarbon radicals containing one double bond and having from 3 to 7 carbon atoms such as, for example, allyl, 3-butenyl, 2-butenyl, 2-pentenyl, 3-pentenyl, methallyl, or 3-methyl-2-butenyl, with allyl and methallyl being preferred; $C_3$-$C_7$alkynyl defines straight and branch chained hydrocarbon radicals containing one triple bond and having from 3 to 7 carbon atoms such as, for example, propargyl, 2-butynyl, 3-butynyl, 2-pentynyl, 3-pentynyl or 4-pentynyl, with propargyl being preferred; $C_3$-$C_7$cycloalkyl is generic to cyclopropyl, cyclobutyl, cyclopentyl, cyclohexyl and cycloheptyl, with cyclopentyl and cyclohexyl being preferred; $C_1$-$C_5$alkyloxy denotes, for example, methoxy, ethoxy, n-propyloxy, isopropyloxy, the four butyloxy isomers or the pentyloxy isomers; $C_1$-$C_7$alkyloxy$C_1$-$C_7$alkyl denotes for example methoxymethyl, methoxyethyl, methoxypropyl, ethoxymethyl, ethoxyethyl, ethoxypropyl, propoxymethyl, propoxyethyl, propoxypropyl, isopropoxymethyl, isopropoxyethyl, isopropoxypropyl, 2-methoxypropyl, 2-ethoxypropyl, 2-methoxybutyl, 3-methoxybutyl, 2-ethoxybutyl, or 3-ethoxybutyl.

As typical examples of aryl $C_1$-$C_5$alkyl there may be mentioned benzyl, phenylethyl, 4-chlorobenzyl, 4-chlorophenylethyl, 4-methoxybenzyl or 3-methoxybenzyl, benzyl being preferred.

As typical examples of C₃-C₇cycloalkyl substituted with one or two C₁-C₅alkyl radicals there may be mentioned 1-methylcyclohexyl, 2-methylcyclohexyl, 2,2-dimethylcyclopropyl, 1-methylcyclopentyl and 1-methylcyclopropyl.

As typical examples of the heterocyclic radicals and the Ar radical as defined hereinabove, there may be mentioned phenyl, 4-methoxyphenyl, 3-methoxyphenyl, 3-methylphenyl, 4-methylphenyl, 2-chlorophenyl, 3-chlorophenyl, 4-chlorophenyl, 3,4-dichlorophenyl, 4-trifluoromethylphenyl, 3-trifluoromethylphenyl, 2-methoxyphenyl, 2-methylphenyl, 2,4-dimethylphenyl, 4-fluorophenyl, 4-bromophenyl, 2,4-dichlorophenyl, 2-chlorophenyl, 2,5-dimethylphenyl, 2-methoxy-5-fluorophenyl, 2-fluoro-5-methylphenyl, 4-nitrophenyl, 2-pyridinyl, 3-pyridinyl, 4-pyridinyl, 2-furanyl, 2-thienyl, naphthalenyl, 2-ethylphenyl or 4-ethylphenyl.

Depending on the nature of the various substituents, e.g. of the nature of the A and Z substituent, the compounds of formula (I) may contain asymmetrical carbon atoms. Unless otherwise mentioned or indicated, the chemical designation of compounds denotes the mixtures of all stereochemically isomeric forms. These mixtures contain all diastereomeres and enantiomeres of the basic molecular structure. Pure isomeric forms of these compounds can be separated from the mixtures by conventional separation methods. Preferably, if a specific stereochemical form is desired, said compound will be synthesized by stereoselective methods of preparation. These methods will advantageously employ optically active starting materials.

The invention also comprises the use of the salts which the compounds of formula (I) are able to form with organic or inorganic bases such as amines, alkali metal bases and earth alkaline metal bases, or quaternary ammonium bases, or with organic or inorganic acids, such as mineral acids, sulfonic acids, carboxylic acids, or phosphorus containing acids.

Examples of salt-forming mineral acids are hydrofluoric acid, hydrochloric acid, hydrobromic acid, hydroiodic acid, sulfuric acid, nitric acid, chloric acid, perchloric acid or phosphoric acid. Preferred salt-forming sulfonic acids are toluenesulfonic acid, benzenesulfonic acid, methanesulfonic acid or trifluoromethane sulfonic acid. Preferred salt-forming carboxylic acids are acetic acid, trifluoroacetic acid, benzoic acid, chloroacetic acid, phthalic acid, maleic acid, malonic acid and citric acid. Phosphorus containing acids are the various phosphonous acids, phosphonic acids and phosphinic acids.

Preferred salt-forming alkali metal hydroxides and earth alkaline metal hydroxides are the hydroxides of lithium, sodium, potassium, magnesium or calcium, most preferably those of sodium or potassium. Examples of suitable salt-forming amines are primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, with isopropylamine, diethanolamine and 1,4-diazabicyclo[2.2.2]octane being most preferred. Examples of quaternary ammonium bases are, in general, the cations of haloammonium salts, e.g. the tetramethylammonium cation, the trimethylbenzylammonium cation, the trieethylbenzylammonium cation, and also the ammonium cation.

As defined hereinabove, the invention also comprises the quaternised forms of the compounds of formula (I), said quaternised forms being represented by the formula

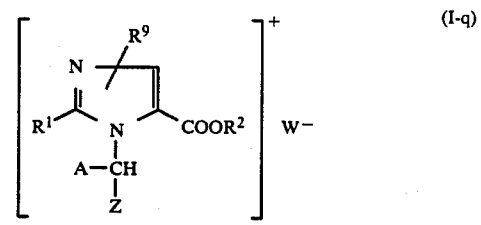

wherein R⁹ is C₁-C₇alkyl optionally substituted with C₁-C₅alkyloxy, C₁-C₅alkylthio, C₁-C₅alkylcarbonyl, C₁-C₅alkyloxycarbonyl, C₁-C₅alkyl, phenyl or phenylcarbonyl; or C₃-C₇alkynyl or C₃-C₇alkenyl optionally substituted with phenyl; said phenyl as used in the definition of R⁹ being optionally substituted with one to three halo, nitro, cyano, C₁-C₅alkyl, C₁-C₅alkyloxy or trifluoromethyl substituents.

Preferably R⁹ is allyl, methallyl, propargyl or C₁-C₄alkyl optionally substituted with C₁-C₅alkyl, phenyl or phenylcarbonyl, said phenyl being optionally substituted with one or two methyl, methoxy or halo radicals.

W is an organic or inorganic anion and preferably is hydroxy, alkyloxy or an anion arising from an acid such as hydrofluoric acid, hydrochloric acid, hydrobromic acid, hydroiodic acid, sulfuric acid, nitric acid, chloric acid, perchloric acid, phosphoric acid, dialkylphosphoric acid, 4-methylbenzenesulfonic acid, benzenesulfonic acid, methanesulfonic acid, trifluoromethylsulfonic acid, acetic acid, trifluoroacetic acid, benzoic acid, chloroacetic acid, phtalic acid, maleic acid, malonic acid, citric acid and more preferably is halo, 4-methylphenylsulfonate, methanesulfonate, 4-bromophenylsulfonate or dialkylphosphate.

Moreover, as defined hereinabove the invention also comprises the N-oxides which the compounds of formula (I) are able to form either in the imidazole moiety or in any N-containing radical possibly making up the structure of the compoundss of formula (I), e.g., A, Ar or Z being pyridine or pyrimidine. Preferably, the N-oxide is located in the imidazole moiety.

A preferred subgroup of active ingredients which can be used in the method of this invention are those compounds of formula (I), wherein R² is hydrogen or C₁-C₇alkyl, A is C₁-C₇alkyl, naphthalenyl, pyridinyl or C₃-C₇cycloalkyl optionally substituted with C₁-C₅alkyl and Z is pyridinyl, phenyl or phenyl substituted with C₁-C₅alkyloxy, C₁-C₅alkyl or halo.

Within this preferred group, those compounds are particularly preferred wherein R² is hydrogen, methyl or ethyl, A is C₃-C₅alkyl, 2-pyridinyl, 3-pyridinyl or 4-pyridinyl and Z is phenyl or phenyl substituted with methoxy, methyl or chloro.

The most preferred compounds which can be used in the method according to this invention are selected among methyl 1-[1-(2-methoxyphenyl)butyl]-1H-imidazole-5-carboxylate, methyl 1-[1-(2-chlorophenyl)-butyl]-1Himidazole-5-carboxylate, methyl 1-[1-(2-methylphenyl)butyl]-1H-imidazole-5-carboxylate, methyl 1-[1-(3-chlorophenyl)butyl]-1H-imidazole-5-carboxylate, methyl 1-[(2-pyridinyl)phenylmethyl]-1H̲- imidazole-5-carboxylate, 1-[1-(2-methoxyphenyl)butyl]-1H-imidazole-5-carboxylic acid, 1-[1-(2-chlorophenyl)butyl]-1H-imidazole-5-carboxylic acid, 1[1-(2-methylphenyl)butyl]-1H-imidazole-5-carboxylic acid, 1-[1-(3-chlorophenyl)butyl]-1H-imidazole-5-carboxylic acid, and 1-[(2-pyridinyl)phenylmethyl]-1H-imidazole-5-carboxylic acid, the salts, and possible stereoisomeric forms thereof.

As mentiond hereinabove most of the active ingredients of formula (I) are novel and have especially been developed to be used as active substances in the method of the present invention. These novel compounds constituting a further aspect of the invention can be represented by the formula

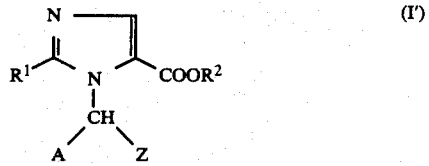

or a stereoisomeric form thereof, or a salt thereof, or a quaternised form thereof, or a N-oxide thereof, wherein
$R^1$ is hydrogen or mercapto;

$R^2$ is hydrogen, $C_1$-$C_7$alkyl, $C_3$-$C_7$alkenyl, $C_3$-$C_7$alkynyl, $C_1$-$C_7$alkyloxy$C_1$-$C_7$alkyl, aryl$C_1$-$C_5$alkyl or $C_3$-$C_7$cycloalkyl; wherein aryl is phenyl optionally substituted with one to three substituents independently selected from $C_1$-$C_5$alkyl, $C_1$-$C_5$alkyloxy and halo;

A is $C_3$-$C_7$cycloalkyl optionally substituted with one or two $C_1$-$C_5$alkyl radicals; $C_3$-$C_7$alkyl; $C_1$-$C_7$alkyl substituted with $C_1$-$C_7$alkyloxy or with an Ar radical; or $C_1$-$C_7$alkyl substituted with both a $C_1$-$C_7$alkyloxy and an Ar radical; or a radical selected from pyridinyl, pyrimidinyl, naphthalenyl, furanyl and thienyl, each unsubstituted or substituted with one or two radicals independently selected from $C_1$-$C_5$alkyl, $C_1$-$C_5$alkyloxy, halo, nitro, amino, mono- and di$C_1$-$C_5$alkylamino, —NH—CO—G, cyano, trifluoromethyl and difluoromethoxy; provided that when A is n-propyl then Z is other than phenyl;

said radical Ar being phenyl, pyridinyl, pyrimidinyl, naphthalenyl, furanyl or thienyl, each unsubstituted or substituted with one or two and in case Ar is phenyl also with three substituents selected from $C_1$-$C_5$alkyl, $C_1$-$C_5$alkyloxy, halo, nitro, amino, mono- and di$C_1$-$C_5$alkylamino, —NH—CO—G, cyano, trifluoromethyl and difluoromethoxy;

Z is naphthalenyl, thienyl, furanyl, pyrimidinyl, phenyl or pyridinyl, each unsubstituted or substituted with one or two substituents and in case Z is phenyl also with three substituents independently selected from $C_1$-$C_5$alkyl, $C_1$-$C_5$alkyloxy, halo, cyano, nitro, amino, mono- and di$C_1$-$C_5$alkylamino, —NH—CO—G, trifluoromethyl and difluoromethoxy; and G is $C_1$-$C_6$alkyl.

Particularly preferred novel compounds are those novel compounds wherein A is $C_3$-$C_7$cycloalkyl optionally substituted with one or two $C_1$-$C_5$alkyl radicals; branched $C_3$-$C_7$alkyl; $C_1$-$C_7$alkyl substituted with $C_1$-$C_7$alkyloxy or with an Ar radical; or $C_1$-$C_7$alkyl substituted with both a $C_1$-$C_7$alkyloxy and an Ar radical; or a radical selected from pyridinyl, pyrimidinyl, naphthalenyl, furanyl and thienyl, each unsubstituted or substituted with one or two radicals independently selected from $C_1$-$C_5$alkyl, $C_1$-$C_5$alkyloxy, halo, nitro, amino, mono- and di$C_1$-$C_5$alkylamino, —N-H—CO—G, cyano, trifluoromethyl and difluoromethoxy.

More particularly preferred novel compounds are those wherein $R^2$ is hydrogen or $C_1$-$C_7$alkyl, A is branched $C_3$-$C_7$alkyl, pyridinyl, naphthalenyl or $C_3$-$C_7$cycloalkyl optionally substituted withh $C_1$-$C_5$alkyl and Z is pyridinyl, phenyl or phenyl substituted with $C_1$-$C_5$alkyloxy, $C_1$-$C_5$alkyl or halo.

Still more particularly preferred novel compounds are those, wherein $R^2$ is hydrogen, methyl or ethyl, A is branched $C_3$-$C_5$-alkyl, 2-pyridinyl, 3-pyridinyl or 4-pyridinyl and Z is phenyl or phenyl substituted with methoxy, methyl or chloro.

The most preferred novel compounds are selected from the group consisting of methyl 1-[1-(2-methoxyphenyl)butyl]-1H-imidazole-5-carboxylate, methyl 1-[1-(3-chlorophenyl)butyl]-1H-imidazole-5-carboxylate, methyl 1-[1-(2-methylphenyl)butyl]-1H-imidazole-5-carboxylate, methyl 1-[1-(3-chlorophenyl)butyl]-1H-imidazole-5-carboxylate, methyl 1-[(2-pyridinyl)-phenylmethyl]-1H-imidazole-5-carboxylate, 1-[1-(2-methoxyphenyl)butyl-1H-imidazole-5-carboxylic acid, 1-[1-(2-chlorophenyl)butyl]-1H-imidazole-5-carboxylic acid, 1-[1(2-methylphenyl)butyl]-1H-imidazole-5-carboxylic acid, 1-[1-(3-chlorophenyl)butyl]-1H-imidazole-5-carboxylic acid, 1-[(2-pyridinyl)phenylmethyl]-1H-imidazole-5-carboxylic acid, the salts and possible stereoisomeric forms thereof.

As used hereinabove the term branched $C_3$-$C_7$alkyl defines branch chained hydrocarbon radicals having from 3 to 7 carbon atoms, i.e. hydrocarbon radicals other than —$(CH_2)_s$H, wherein s is an integer of from 3 to 7.

The preparation of the compounds of formula (I), both the novel ones and the known ones, is generally carried out by the following methods.

The compounds of formula (I) can be obtained by condensing a compound of formula

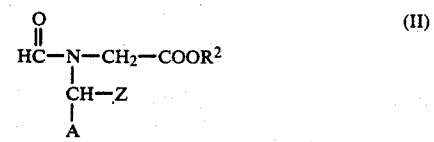

wherein $R^2$, A and Z are as defined hereinabove, with a $C_1$-$C_4$alkyl ester of formic acid in the presence of suitable base such as, for example, an alkali metal alkoxide or hydride, e.g. sodium methoxide, potassium ethoxide, sodium hydride, lithium hydride, and the like, in a reaction-inert solvent; and treating the resultant intermediate of formula

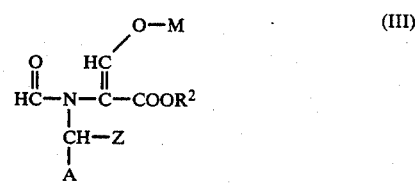

wherein $R^2$, A and Z are as defined hereinabove and M is an alkali metal atom.

(a) with an alkali metal isothiocyanate in the presence of an acid, thus obtaining a 2-mercaptoimidazole of formula

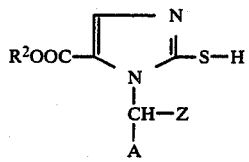

(Ia)

wherein R², A and Z are as defined hereinabove, which optionally is converted into a compound of the formula

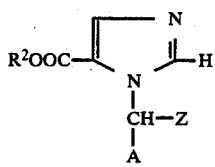

(Ib)

by reacting the starting compound with sodium nitrite in the presence of nitric acid in an aqueous medium; or with Raney-nickel in the presence of a lower aliphatic alcohol, preferably ethanol, at a temperature between 40° C. and 80° C.; or also by treating the starting compounds with an aqueous hydrogen peroxide solution preferably in the presence of a carboxylic acid, e.g. acetic acid; or (b) with a carboxylic acid amide of 1 to 3 carbon atoms, preferably formamide, in the presence of an acid at a temperature between 50° C. and 250° C., preferably between 120° C.; and 170° C.; or (c) with an excess of ammonium carbonate or hydrogen carbonate in a suitable solvent, which may be a reaction-inert solvent or an acid, at a temperature between 20° C. and 200° C., preferably between 25° C. and the reflux temperature of the reaction mixture.

In the afore-mentioned processes reaction-inert solvents are, for example, aromatic hydrocarbons such as benzene, methylbenzene or dimethylbenzene; ethers such as, for example, diethylether, tetrahydrofuran or dioxane; or other aprotic organic solvents. For the cyclization-reaction of the imidazole ring structure, strong mineral acids such as hydrohalic acids, e.g. hydrochloric acid, are most conveniently employed. In the ring-forming variant c) also other acids, e.g. acetic acid, can be used. In this reaction an excess of acid of 5 to 50, preferably of 15 to 40 times the required molar amount is most preferably used. The excess of ammonium salt in this process is 2 to 50, preferably 10 to 30 times the required molar amount.

The quaternised forms of the compounds of formula (I) can conveniently be prepared by reacting a compound of formula (I) with a reagent of formula $$R^9\text{---}W^1 \qquad (VII),$$

wherein R⁹ is as defined hereinabove and W¹ is an appropriate leaving group such as, for example, halo, e.g. chloro, bromo, iodo; an alkyl- or arylsulfonyloxy group, e.g. methylsulfonyloxy, 4-methylphenylsulfonyloxy or 4-bromophenylsulfonyloxy; or a dialkylphosphate group; thus preparing those quaternary compounds of formula (I-q) as defined hereinabove, wherein W is W¹. The reaction of (I) with (VII) is preferably conducted in a suitable solvent such as, for example, a hydrocarbon, e.g. hexane, heptane, benzene, methylbenzene, dimethylbenzene and the like; an alcohol, e.g. methanol, ethanol, 2-propanol, 1-butanol and the like; and ether, e.g. 1,1'-oxybisethane, tetrahydrofuran, 1,4-dioxane and the like; a halogenated hydrocarbon, e.g. tetrachloromethane, trichloromethane, dichloromethane and the like; a dipolar aprotic solvent; e.g. N,N-dimethylformamide, N,N-dimethylacetamide, dimethyl sulfoxide, acetonitrile and the like. In some instances, it may be appropriate to conduct the reaction at elevated temperatures. If desired, the anion W¹ in the products obtained according to the above procedures can be exchanged for another anion thus obtaining the other quaternary salts of formula (I-q). Such anion-exchange reaction can conveniently be performed following art-known procedures, e.g. by using an anionic exchanger column, or by converting the quaternary imidazolium salt into the corresponding hydroxide with a basic anion exchanger and subsequently reacting said hydroxide with the appropriate acid.

The N-oxides of the compounds of formula (I) can conveniently be prepared by N-oxidating a compound of formula (I). Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxde, barium peroxide and the like; appropriate organic peroxides may comprise peroxy acids such as, for example, benzenecarboperoxoic acid or halo substituted benzenecarboperoxoic acid, e.g. 3-chlorobenzenecarboperoxoic acid and the like, peroxoalkanoic acids, e.g. peroxoacetic acid the like, alkylhydroperoxides, e.g. t.butyl hydroperoxide and the like. If desired, said N-oxidation may be carried out in a suitable solvent such as, for example, water, a lower alkanol, e.g. methanol, ethanol, propanol, butanol and the like, a hydrocarbon, e.g. benzene, methylbenzene, dimethylbenzene and the like, a ketone, e.g. 2-propanone, 2-butanone and the like, a halogenated hydrocarbon, e.g. dichloromethane, trichloromethane and the like, and mixtures of such solvents. In order to enhance the reaction rate, it may be appropriate to heat the reaction mixture.

The compounds of formula (I) can also be converted into each other following art-known functional groups-transformation reactions.

The substituent R² on the carboxylic acid group may be transformed to other substituents encompassed by the definition of R² by suitable reactions known in the art for the modification of carboxylic acid functions, e.g. by hydrolysis and esterification and/or transesterification.

If the synthesis of sterochemically pure isomers is intended, stereoselective reaction steps and conditions are recommended. On the other hand, conventional methods of separation can be used for obtaining pure isomers from a mixture of stereochemical isomers.

The starting materials for the preparation of the novel compounds of formula (I) are known, or they can be obtained by known synthesis procedures.

For example, the compounds of formula (II) can be obtained by reacting a glycine ester of formula

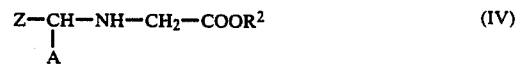

(IV)

wherein R², A and Z are as defined hereinabove, with formic acid in the presence of acetic anhydride. In turn, the compounds of formula (IV) can be prepared by reacting an amine of formula

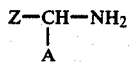 (V)

wherein A and Z are as defined under formula (I), with a α-haloacetic acid ester, e.g. α-bromoacetic ester, of formula

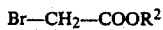 (VI)

wherein $R^2$ is as defined under formula (I), in the presence of an acid-binding agent, such as sodium carbonate.

The compounds of formula (I) are stable compounds and no precautionary measures are required for handling them.

When used at the indicated rates of application, the compounds of formula (I) have good selective herbicidal properties which make them most suitable for use in crops of useful plants, preferably in maize and in rice. In some cases damage is also caused to weeds which up to now have only been controlled with total herbicides.

At higher rates of application, all tested plants are so severely damaged in their development that they die.

The invention also relates to herbicidal compositions containing one or more inert carriers and, if desired, other adjuvants and as an active ingredient a herbicidally effective amount of a compound of formula (I) as defined hereinabove. Preferred compositions contain as active ingredient a novel compound of formula (I), while preferred methods of controlling weeds make use of the novel compounds.

In the method for controlling weeds according to the invention the compounds of formula (I) are used in unmodified form or, preferably, together with the adjuvants conventionally employed in the art of formulation. They are therefore formulated following art-known procedures to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula (I) and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are aromatic hydrocarbons, preferably the fractions containing 8 to 12 carbon atoms, e.g. dimethylbenzene mixtures or substituted naphthalenes, phthalates such as dibutyl phthalate or dioctyl phthalate, aliphatic or alicyclic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula (I) to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, earth alkaline metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. In addition, there may also be mentioned fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, earth alkaline metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzene sulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (alifatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyethylene sorbitan, such as polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annular", MC Publishing Corp., Ridgewood, N.J., 1981; H. Stache, "Tensid-Taschenbuch", 2nd Edition, C. Hanser Verlag, Munich & Vienna, 1981, M. and J. Ash, "Encyclopedia of Surfactants", Vol. I–III, Chemical Publishing Co., New York, 1980–81.

The herbicidal compositions which are preferably employed in the method of the invention usually contain 0.1 to 95%, preferably 0.1 to 80%, of a compound of formula (I), 1 to 99.9%, of a solid or liquid adjuvant, and 0 to 25%, preferably 0.1 to 25%, of a surfactant.

Preferred formulations are composed in particular of the following constituents (%=percentage by weight):

| Emulsifiable concentrates | | |
|---|---|---|
| active ingredient: | 1 to 20%, | preferably 5 to 10% |
| surfactant: | 5 to 30%, | preferably 10 to 20% |
| liquid carrier: | 50 to 94%, | preferably 70 to 85% |
| Dusts | | |
| active ingredient: | 0.1 to 10%, | preferably 0.1 to 1% |
| solid carrier: | 99.9 to 90%, | preferably 99.9 to 99% |
| Suspension concentrates | | |
| active ingredient: | 5 to 75%, | preferably 10 to 50% |
| water: | 94 to 25%, | preferably 88 to 30% |
| surfactant: | 1 to 40%, | preferably 2 to 30% |
| Wettable powders | | |
| active ingredient: | 0.5 to 90%, | preferably 1 to 80% |
| surfactant: | 0.5 to 20%, | preferably 1 to 15% |
| solid carrier: | 5 to 95%, | preferably 15 to 90% |
| Granulates | | |
| active ingredient: | 0.5 to 30%, | preferably 3 to 15% |
| solid carrier: | 99.5 to 70%, | preferably 97 to 85% |

Some of the compounds of the formula (I) which are used as active ingredients in the method for controlling weeds in accordance with the invention are listed in the following tables with the purpose of illustrating and not to limiting it thereto.

TABLE 1

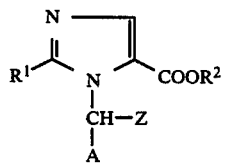

| Comp. No. | $R^1$ | $R^2$ | A | Z | physical data |
|---|---|---|---|---|---|
| 1.01 | H | $CH_3$ | $CH_3$ | $C_6H_5-$ | .HCl/m.p. 172–174° C. |
| 1.02 | H | $CH_3$ | $CH_3$ | 4-$OCH_3-C_6H_4-$ | .HCl/m.p. 130–131° C. |
| 1.03 | H | $CH_3$ | $C_3H_7-n$ | $C_6H_5-$ | .HCl/m.p. 150–152° C. |
| 1.04 | H | $CH_3$ | $CH_3$ | 4-$CH_3-C_6H_4-$ | .HCl/m.p. 167–168° C. |
| 1.05 | H | $CH_3$ | $CH_3$ | 3-$CH_3-C_6H_4-$ | |
| 1.06 | H | $C_2H_5$ | $C_2H_5$ | $C_6H_5-$ | .HCl/m.p. 169–170.5° C. |
| 1.07 | H | $CH_3$ | $CH_3$ | 3-$Cl-C_6H_4-$ | .HCl/m.p. 151–153.5° C. |
| 1.08 | H | $C_4H_9-n$ | $CH_3$ | $C_6H_5-$ | m.p. 139–141.5° C. |
| 1.09 | H | $C_4H_9-i$ | $CH_3$ | $C_6H_5-$ | |
| 1.10 | H | $C_2H_5$ | $CH_3$ | $C_6H_5-$ | .HCl/m.p. 142–142.8° C. |
| 1.11 | H | $CH_3$ | H | $C_6H_5-$ | .HCl/m.p. 178–178.5° C. |
| 1.12 | H | $CH_3$ | H | 3-Cl-4-$Cl-C_6H_3-$ | |
| 1.13 | H | $CH_3$ | $C_3H_7-n$ | 4-$CF_3-C_6H_4-$ | .HNO$_3$/m.p. 128–128.5° C. |
| 1.14 | H | $CH_3$ | $CH_3$ | 2-Cl-4-$Cl-C_6H_3-$ | |
| 1.15 | H | $CH_3$ | $C_3H_7-n$ | 4-$CH_3-C_6H_4-$ | .HNO$_3$/m.p. 141–143° C. |
| 1.16 | H | $CH_3$ | $C_3H_7-n$ | 3-$CF_3-C_6H_4-$ | m.p. 81–84° C. |
| 1.17 | H | $CH_3$ | $C_3H_7-n$ | 4-$Cl-C_6H_4-$ | .HNO$_3$/m.p. 125.4° C. |
| 1.18 | H | $CH_3$ | $C_3H_7-n$ | 2-$OCH_3-C_6H_4-$ | m.p. 77–78° C. |
| 1.19 | H | $CH_3$ | $C_2H_5$ | 4-$CH_3-C_6H_4-$ | .HNO$_3$/m.p. 132–134° C. |
| 1.20 | H | $CH_3$ | $C_2H_5$ | 4-$OCH_3-C_6H_4-$ | resin |
| 1.21 | H | $CH_3$ | $C_3H_7-n$ | 2-$CH_3-C_6H_4-$ | .HNO$_3$/m.p. 122–123° C. |
| 1.22 | H | $CH_3$ | $C_3H_7-n$ | 3-$CH_3-C_6H_4-$ | resin |
| 1.23 | H | $CH_3$ | $C_2H_5$ | 2-$CH_3$-4-$CH_3-C_6H_3-$ | viscous oil |
| 1.24 | H | $CH_3$ | $C_3H_7-n$ | 4-$F-C_6H_4-$ | .HNO$_3$/m.p. 121.9° C. |
| 1.25 | H | $CH_3$ | $C_3H_7-n$ | 2-$CH_3$-4-$CH_3-C_6H_3-$ | viscous oil |
| 1.26 | H | $CH_3$ | $C_3H_7-n$ | 2-Cl-4-$Cl-C_6H_3-$ | m.p. 122–123° C. |
| 1.27 | H | $CH_3$ | $C_3H_7-n$ | 3-$Cl-C_6H_4-$ | .HNO$_3$/m.p. 108.5° C. |
| 1.28 | H | $CH_3$ | $C_3H_7-n$ | 4-$Cl-C_6H_4-$ | |
| 1.29 | H | $CH_3$ | $C_3H_7-n$ | 2-$Cl-C_6H_4-$ | .HNO$_3$/m.p. 123.1° C. |
| 1.30 | H | $CH_3$ | $C_5H_{11}-n$ | 4-$CH_3-C_6H_4-$ | .HNO$_3$/m.p. 120–125° C. |
| 1.31 | H | $CH_3$ | $C_3H_7-n$ | 2-$OCH_3$-5-$F-C_6H_3-$ | resin |
| 1.32 | H | $CH_3$ | $C_3H_7-n$ | 2-F-5-$CH_3-C_6H_3-$ | .HNO$_3$/solid |
| 1.33 | H | $CH_3$ | $C_3H_7-n$ | 2-$CH_3$-5-$CH_3-C_6H_3-$ | .HNO$_3$/m.p. 149–150° C. |
| 1.34 | H | $CH_3$ | $C_5H_{11}-n$ | $C_6H_5-$ | .HNO$_3$/m.p. 143–145° C. |
| 1.35 | H | $CH_3$ | $C_4H_9-n$ | $C_6H_5-$ | .HNO$_3$/m.p. 142–143° C. |

TABLE 1-continued

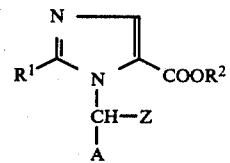

| Comp. No. | R[1] | R[2] | A | Z | physical data |
|---|---|---|---|---|---|
| 1.36 | H | $CH_3$ | $C_4H_9-n$ | $4-CH_3-C_6H_4-$ | .$HNO_3$/m.p. 122° C.(dec.) |
| 1.37 | SH | $CH_3$ | $CH_3$ | $C_6H_5-$ | m.p. 131-134° C. |
| 1.38 | SH | $CH_3$ | H | $C_6H_5-$ | |
| 1.39 | SH | $CH_3$ | H | $3-Cl-4-Cl-C_6H_3-$ | |
| 1.40 | SH | $CH_3$ | $C_3H_7-n$ | $4-CF_3-C_6H_4-$ | m.p. 193-193.5° C. |
| 1.41 | SH | $CH_3$ | $C_3H_7-n$ | $4-CH_3-C_6H_4-$ | m.p. 209-211° C. |
| 1.42 | SH | $CH_3$ | $C_3H_7-n$ | $2-OCH_3-C_6H_4-$ | m.p. 156-158° C. |
| 1.43 | SH | $CH_3$ | $C_3H_7-n$ | $3-CF_3-C_6H_4-$ | m.p. 108-111° C. |
| 1.44 | SH | $CH_3$ | $C_2H_5$ | $4-OCH_3-C_6H_4-$ | m.p. 141-144° C. |
| 1.45 | SH | $CH_3$ | $C_2H_5$ | $4-CH_3-C_6H_4-$ | m.p. 221-223° C. |
| 1.46 | SH | $CH_3$ | $C_3H_7-n$ | $2-Cl-4-Cl-C_6H_3-$ | m.p. 58-61° C. |
| 1.47 | SH | $CH_3$ | $C_2H_5$ | $2-CH_3-4-CH_3-C_6H_3-$ | m.p. 150-153° C. |
| 1.48 | SH | $CH_3$ | $C_3H_7-n$ | $2-CH_3-4-CH_3-C_6H_3-$ | solid |
| 1.49 | SH | $CH_3$ | $C_5H_{11}-n$ | $4-CH_3-C_6H_4-$ | m.p. 94-101° C. |
| 1.50 | SH | $CH_3$ | $C_3H_7-n$ | $3-CH_3-C_6H_4-$ | m.p. 131-134° C. |
| 1.51 | SH | $CH_3$ | $C_3H_7-n$ | $2-OCH_3-5-F-C_6H_3-$ | m.p. 174-176° C. |
| 1.52 | SH | $CH_3$ | $C_3H_7-n$ | $2-F-5-CH_3-C_6H_3-$ | m.p. 125-127° C. |
| 1.53 | SH | $CH_3$ | $C_3H_7-n$ | $2-CH_3-C_6H_4-$ | m.p. 171-173° C. |
| 1.54 | SH | $CH_3$ | $C_3H_7-n$ | $3-CH_3-C_6H_4-$ | solid |
| 1.55 | SH | $CH_3$ | $C_5H_{11}-n$ | $C_6H_5-$ | m.p. 108-109° C. |
| 1.56 | SH | $CH_3$ | $C_4H_9-n$ | $C_6H_5-$ | m.p. 143-144° C. |
| 1.57 | H | $CH_3$ | 2-pyridinyl | $C_6H_5-$ | .$HNO_3$/m.p. 137.6° C. |
| 1.58 | H | $CH_3$ | 2-naphtalenyl | $C_6H_5$ | m.p. 96° C. |
| 1.59 | H | $CH_3$ | 2-pyridinyl | 2-pyridinyl | |
| 1.60 | H | $CH_3$ | 3-pyridinyl | $C_6H_5-$ | |
| 1.61 | H | $CH_3$ | 4-pyridinyl | $C_6H_5-$ | m.p. 137.8° C. |
| 1.62 | H | $CH_3$ | 2-pyrimidinyl | $C_6H_5-$ | |
| 1.63 | H | $CH_3$ | 2-furanyl | $C_6H_5-$ | |
| 1.64 | H | $CH_3$ | 2-thienyl | $C_6H_5-$ | |
| 1.65 | H | $CH_3$ | 2-thienyl | $4-F-C_6H_4-$ | |
| 1.66 | H | $CH_3$ | 2-pyridinyl | $4-Cl-C_6H_4-$ | |
| 1.67 | H | $CH_3$ | 4-pyridinyl | $4-F-C_6H_4-$ | |
| 1.68 | H | $CH_3$ | $C_3H_7-i$ | $4-CH_3-C_6H_4-$ | resin |
| 1.69 | H | $CH_3$ | $C_3H_7-i$ | $4-OCH_3-C_6H_4-$ | resin |
| 1.70 | H | $CH_3$ | $C_4H_9-t$ | $C_6H_5-$ | |
| 1.71 | H | $CH_3$ | $C_4H_9-t$ | $2-CH_3-C_6H_4-$ | |
| 1.72 | H | $CH_3$ | $C_4H_9-t$ | $3-CH_3-C_6H_4-$ | |
| 1.73 | H | $CH_3$ | $C_4H_9-t$ | $4-CH_3-C_6H_4-$ | |
| 1.74 | H | $CH_3$ | $C_4H_9-t$ | $2-C_2H_5-C_6H_4-$ | |
| 1.75 | H | $CH_3$ | $C_4H_9-t$ | $3-CH_3-4-CH_3-C_6H_3-$ | |
| 1.76 | H | $CH_3$ | 1-methylcyclohexyl | $C_6H_5-$ | |
| 1.77 | H | $CH_3$ | $-C(CH_3)_2-C_2H_5$ | $C_6H_5-$ | |
| 1.78 | H | $CH_3$ | cyclohexyl | $C_6H_5-$ | m.p. 95-97° C. |
| 1.79 | SH | $CH_3$ | $C_3H_7-i$ | $4-CH_3-C_6H_4-$ | m.p. 171-173° C. |
| 1.80 | SH | $CH_3$ | $C_3H_7-i$ | $4-OCH_3-C_6H_4-$ | m.p. 110-112° C. |
| 1.81 | SH | $CH_3$ | $C_4H_9-t$ | $C_6H_5-$ | m.p. 194-196° C. |
| 1.82 | SH | $CH_3$ | $C_4H_9-t$ | $2-CH_3-C_6H_4-$ | |
| 1.83 | SH | $CH_3$ | $C_4H_9-t$ | $3-CH_3-C_6H_4-$ | |
| 1.84 | SH | $CH_3$ | $C_4H_9-t$ | $4-CH_3-C_6H_4-$ | |
| 1.85 | SH | $CH_3$ | $C_4H_9-t$ | $2-C_2H_5-C_6H_4-$ | |
| 1.86 | SH | $CH_3$ | $C_4H_9-t$ | $3-CH_3-4-CH_3-C_6H_3-$ | |
| 1.87 | SH | $CH_3$ | 1-methylcyclohexyl | $C_6H_5-$ | |
| 1.88 | SH | $CH_3$ | $-C(CH_3)_2-C_2H_5$ | $C_6H_5-$ | |
| 1.89 | SH | $CH_3$ | cyclohexyl | $C_6H_5-$ | m.p. 180-182° C. |
| 1.90 | H | $C_2H_5$ | $C_3H_7-n$ | 2-pyridinyl | |
| 1.91 | SH | $C_2H_5$ | $C_3H_7-n$ | 2-pyridinyl | |
| 1.92 | H | $CH_2CH=CH_2$ | $C_3H_7-i$ | $C_6H_5-$ | |
| 1.93 | SH | $CH_2CH=CH_2$ | $C_3H_7-i$ | $C_6H_5-$ | |
| 1.94 | H | $C_6H_{13}-n$ | $CH_3$ | $3-Cl-C_6H_4-$ | |
| 1.95 | SH | $C_6H_{13}-n$ | $CH_3$ | $3-Cl-C_6H_4-$ | |
| 1.96 | H | $C_6H_{11}$cyc. | $CH_3$ | $4-Cl-C_6H_4-$ | |
| 1.97 | SH | $C_6H_{11}$cyc. | $CH_3$ | $4-Cl-C_6H_4-$ | |
| 1.98 | H | $CH_2-C\equiv CH$ | $C_2H_5$ | $C_6H_5-$ | |
| 1.99 | SH | $CH_2-C\equiv CH$ | $C_2H_5$ | $C_6H_5-$ | |
| 1.100 | H | $CH_2-C\equiv CH$ | $C_4H_9-t$ | 2-pyridinyl | |
| 1.101 | SH | $CH_2-C\equiv CH$ | $C_4H_9-t$ | 2-pyridinyl | |
| 1.102 | H | $CH_2-CH=CH_2$ | $C_3H_7-i$ | $4-OCH_3-C_6H_4-$ | |
| 1.103 | SH | $CH_2-CH=CH_2$ | $C_3H_7-i$ | $4-OCH_3-C_6H_4-$ | |
| 1.104 | H | $CH_3$ | $C_3H_7-n$ | $4-NO_2-C_6H_4-$ | |
| 1.105 | SH | $CH_3$ | $C_3H_7-n$ | $4-NO_2-C_6H_4-$ | |
| 1.106 | H | $CH_3$ | $C_3H_7-i$ | $4-NO_2-C_6H_4-$ | |

TABLE 1-continued

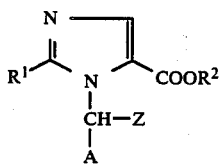

| Comp. No. | R¹ | R² | A | Z | physical data |
|---|---|---|---|---|---|
| 1.107 | SH | $CH_3$ | $C_3H_7$—i | 4-$NO_2$—$C_6H_4$— | |
| 1.108 | H | $CH_3$ | $C_4H_9$—i | 4-$NH_2$—$C_6H_4$— | |
| 1.109 | SH | $CH_3$ | $C_4H_9$—i | 4-$NH_2$—$C_6H_4$— | |
| 1.110 | H | $C_2H_5$ | $C_3H_7$—i | 4-$CH_3CONH$—$C_6H_4$— | |
| 1.111 | SH | $C_2H_5$ | $C_3H_7$—i | 4-$CH_3CONH$—$C_6H_4$— | |
| 1.112 | H | H | H | $C_6H_5$— | .HCl/m.p. 211–215° C. |
| 1.113 | H | H | $CH_3$ | $C_6H_5$— | m.p. 187–189° C. |
| 1.114 | H | $CH_3$ | $CH_3$ | 4-Cl—$C_6H_4$— | .HCl/m.p. 147–148° C. |
| 1.115 | H | $CH_3$ | $C_2H_5$ | $C_6H_5$— | .HCl/m.p. 167–168.5° C. |
| 1.116 | H | $C_3H_7$—n | $CH_3$ | $C_6H_5$— | .HCl/m.p. 156–157° C. |
| 1.117 | H | $C_3H_7$—i | $CH_3$ | $C_6H_5$— | .HCl/m.p. 192–193.5° C. |
| 1.118 | H | $CH_3$ | $CH_3$ | 4-Br—$C_6H_4$— | .HCl/m.p. 137–139° C. |
| 1.119 | H | $CH_3$ | $CH_3$ | 4-F—$C_6H_4$— | .HCl/m.p. 174–175.5° C. |
| 1.120 | H | $CH_3$ | $CH_3$ | 3-$CH_3$—4-$CH_3$—$C_6H_3$— | .HCl/m.p. 166–167° C. |
| 1.121 | H | $CH_2$—C≡CH | $CH_3$ | $C_6H_5$— | m.p. 92–93° C. |
| 1.122 | H | $CH_3$ | $CH_3$ | 2-Cl—$C_6H_4$— | .HCl/m.p. 181–183° C. |
| 1.123 | H | $CH_2$—CH=$CH_2$ | $CH_3$ | $C_6H_5$— | .HCl/m.p. 134–136° C. |
| 1.124 | H | $C_5H_{11}$—n | $CH_3$ | $C_6H_5$— | .HCl/m.p. 139–140° C. |
| 1.125 | H | $CH_3$ | $CH_3$ | 3-pyridinyl | .2HCl/m.p. 178–189° C.(dec.) |
| 1.126 | H | H | $C_2H_5$ | $C_6H_5$— | .HCl/m.p. 142–151° C.(dec.) |
| 1.127 | H | $CH_3$ | $CH_3$ | 4-pyridinyl | m.p. 79–80° C. |
| 1.128 | H | $CH_3$ | $CH_3$ | 2-pyridinyl | .2HCl/m.p. 183.5–186.5° C. |
| 1.129 | H | H | $CH_3$ | 4-Cl—$C_6H_4$— | m.p. 188–189° C. |
| 1.130 | H | H | $CH_3$ | 4-$CH_3$—$C_6H_4$— | m.p. 191.5–193° C. |
| 1.131 | H | H | $CH_3$ | 3-Cl—$C_6H_4$— | m.p. 165.5–167.5° C. |
| 1.132 | H | H | $CH_3$ | 2-Cl—$C_6H_4$— | m.p. 224–225.5° C. |
| 1.133 | H | H | $CH_3$ | 3-$CH_3$—4-$CH_3$—$C_6H_3$— | m.p. 216–218° C. |
| 1.134 | H | H | $CH_3$ | 4-Br—$C_6H_4$— | m.p. 193–194.5° C.(dec.) |
| 1.135 | H | H | $CH_3$ | 4-$CH_3O$—$C_6H_4$— | m.p. 144.5–148° C. |
| 1.136 | H | H | $CH_3$ | 4-F—$C_6H_4$— | m.p. 190.5–194° C.(dec.) |
| 1.137 | H | $C_3H_7$—i | $CH_3$ | 4-F—$C_6H_4$— | .HCl/m.p. 190–191.5° C. |
| 1.138 | H | $C_2H_5$ | $CH_3$ | $C_6H_5$— | picrate/m.p. 114–115.5° C. |
| 1.139 | H | $C_2H_5$ | $CH_3$ | 4-F—$C_6H_4$— | .HCl/m.p. 113–114° C. |
| 1.140 | H | $CH_2$—CH=CH—$CH_3$ | $CH_3$ | $C_6H_5$— | .HCl/m.p. 139–140.5° C. |
| 1.141 | H | $C_2H_5$ | $CH_3$ | $C_6H_5$— | m.p. 49–51° C. |
| 1.142 | H | H | $CH_3$ | 2-pyridinyl | m.p. 212–215° C. |
| 1.143 | H | cyclohexyl | $CH_3$ | $C_6H_5$— | .HCl/m.p. 179–182° C.(dec.) |
| 1.144 | H | $C_2H_5$ | $CH_3$ | 2-pyridinyl | .2HCl/m.p. 181.5–184° C. |
| 1.145 | H | $C_3H_7$—n | $CH_3$ | $C_6H_5$— | .$HNO_3$/m.p. 119.1–119.9° C. |
| 1.146 | H | $C_2H_5$ | $CH_3$ | $C_6H_5$— | .$HNO_3$/m.p. 138–139° C. |
| 1.147 | H | $C_2H_5$ | $CH_3$ | 4-$NO_2$—$C_6H_4$— | .$HNO_3$/m.p. 128–138° C. |
| 1.148 | H | $CH_3$ | $CH_3$ | $C_6H_5$— | m.p. 72–74° C. |
| 1.149 | H | $C_2H_5$ | $CH_3$ | $C_6H_5$— | (+)—R—$HNO_3$/m.p. 117.5° C. |
| 1.150 | H | $C_2H_5$ | $CH_3$ | $C_6H_5$— | (−)—S—$HNO_3$/m.p. 116.5° C. |
| 1.151 | H | $C_2H_5$ | $CH_3$ | $C_6H_5$— | (+)—R/m.p. 67° C. |
| 1.152 | H | $C_2H_5$ | $CH_3$ | $C_6H_5$— | (+)—R—HCl/m.p. 136.5° C. |
| 1.153 | H | $C_2H_5$ | $CH_3$ | $C_6H_5$— | (+)—R—$H_2SO_4$/m.p. 112.4° C. |
| 1.154 | H | $C_2H_5$ | $CH_3$ | $C_6H_5$— | (+)—R—$H_3PO_4$/m.p. 100.6° C. |
| 1.155 | H | H | $CH_3$ | $C_6H_5$— | (+)—R/m.p. 155.8° C. |
| 1.156 | H | H | $CH_3$ | $C_6H_5$— | (+)-(+)—$C_6H_5$—CH—$NH_2$/m.p. 190.3° C. (CH₃) |
| 1.157 | H | H | $CH_3$ | $C_6H_5$— | (−)-(−)—$C_6H_5$—CH—$NH_2$/m.p. 194° C. (CH₃) |
| 1.158 | H | $CH_3$ | $CH_3$ | $C_6H_5$— | (−)—$H_2SO_4$/m.p. 97.8° C. |
| 1.159 | H | $C_3H_7$—n | $CH_3$ | $C_6H_5$— | (−)—$H_2SO_4$.$H_2O$/m.p. 73.3° C. |
| 1.160 | H | $C_3H_7$—n | $CH_3$ | $C_6H_5$— | (+)—$H_2SO_4$.$H_2O$/m.p. 106° C. |
| 1.161 | H | $CH_3$ | $CH_3$ | $C_6H_5$— | (+)—$H_2SO_4$/m.p. 103.8° C. |
| 1.162 | H | $C_2H_5$ | $CH_3$ | $C_6H_5$— | (−)—$H_2SO_4$ |
| 1.163 | H | $CH_3$ | $CH_3$ | $C_6H_5$— | (±)—$H_2SO_4$.$H_2O$/m.p. 136.3° C. |
| 1.164 | H | $CH_3$ | $CH_3$ | $C_6H_5$— | (±)—$H_2SO_4$/m.p. 130.5–131.6° C. |
| 1.165 | H | $C_2H_5$ | $CH_3$ | $C_6H_5$— | (−)/m.p. 68° C. |
| 1.166 | H | H | $CH_3$ | $C_6H_5$— | (+)—R—NaOH/m.p. >300° C. |
| 1.167 | H | $C_2H_5$ | $CH_3$ | 4-F—$C_6H_4$— | (+)—$H_2SO_4$/m.p. 140.6° C. |
| 1.168 | H | $C_2H_5$ | $CH_3$ | 4-F—$C_6H_4$— | (−)—$H_2SO_4$/m.p. 142.3° C. |

TABLE 1-continued

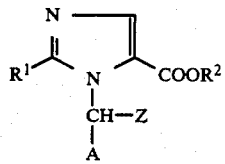

| Comp. No. | R¹ | R² | A | Z | physical data |
|---|---|---|---|---|---|
| 1.169 | H | H | $CH_3$ | $4\text{-}Br\text{-}C_6H_4\text{-}$ | $(+)\text{-}R(-)\text{-}C_6H_5\text{-}CH\text{-}NH_2$ <br> $\vert$ <br> $CH_3$ |
| 1.170 | H | $C_2H_5$ | $CH_3$ | $4\text{-}Br\text{-}C_6H_4\text{-}$ | $(+)\text{-}R\text{-}H_2SO_4$/m.p. 178.1° C. |
| 1.171 | H | $C_2H_5$ | $CH_3$ | $C_6H_5\text{-}$ | $(+)\text{-}[R\text{-}(R^*,R^*)]\text{-}2,3\text{-}$ dihydroxybutanedioate. $H_2O$/m.p. 113.1° C. |
| 1.172 | H | $CH_3$ | $C_3H_7\text{-}n$ | $2\text{-}Cl\text{-}4\text{-}Cl\text{-}C_6H_3\text{-}$ | $.HNO_3$/m.p. 139.3° C. |
| 1.173 | H | $CH_3$ | $C_3H_7\text{-}n$ | $3\text{-}Cl\text{-}4\text{-}Cl\text{-}C_6H_3\text{-}$ | $.HNO_3$/m.p. 107.8° C. |
| 1.174 | H | $CH_3$ | $C_3H_7\text{-}n$ | $2\text{-}Cl\text{-}5\text{-}Cl\text{-}C_6H_3\text{-}$ | $.HNO_3$/m.p. 159.5° C. |
| 1.175 | H | $CH_3$ | 1-naphthalenyl | $C_6H_5\text{-}$ | m.p. 176.2° C. |
| 1.176 | H | $C_2H_5$ | $CH_3$ | $2\text{-}Br\text{-}C_6H_4\text{-}$ | $(-)\text{-}R\text{-}H_2SO_4$/m.p. 118.7° C. |
| 1.177 | SH | $CH_3$ | $CH_3$ | $4\text{-}Cl\text{-}C_6H_4\text{-}$ | m.p. 161-162° C. |
| 1.178 | SH | $CH_3$ | $C_2H_5$ | $C_6H_5\text{-}$ | m.p. 209-210° C. |
| 1.179 | SH | $CH_3$ | $CH_3$ | $4\text{-}Br\text{-}C_6H_4\text{-}$ | m.p. 157-161° C. |
| 1.180 | SH | $CH_3$ | $CH_3$ | $4\text{-}CH_3O\text{-}C_6H_4\text{-}$ | m.p. 139.5-141° C. |
| 1.181 | SH | $CH_3$ | $C_3H_7\text{-}n$ | $C_6H_5\text{-}$ | m.p. 175-177° C. |
| 1.182 | SH | $CH_3$ | $CH_3$ | $4\text{-}F\text{-}C_6H_4\text{-}$ | m.p. 134-136° C. |
| 1.183 | SH | $CH_3$ | $CH_3$ | $4\text{-}CH_3\text{-}C_6H_4\text{-}$ | m.p. 163-165° C. |
| 1.184 | SH | $CH_3$ | $CH_3$ | $3\text{-}CH_3\text{-}4\text{-}CH_3\text{-}C_6H_3\text{-}$ | m.p. 136-138° C. |
| 1.185 | SH | $CH_3$ | $CH_3$ | $2\text{-}Cl\text{-}C_6H_4\text{-}$ | m.p. 183.5-186.5° C. |
| 1.186 | SH | $CH_3$ | $CH_3$ | $3\text{-}Cl\text{-}C_6H_4\text{-}$ | m.p. 178.5-180.5° C. |
| 1.187 | SH | $CH_3$ | $CH_3$ | 3-pyridinyl | m.p. 201-202° C. |
| 1.188 | SH | $C_2H_5$ | $CH_3$ | $C_6H_5\text{-}$ | m.p. 129.8-130.8° C. |
| 1.189 | SH | $CH_3$ | $CH_3$ | 4-pyridinyl | m.p. 181-184° C. |
| 1.190 | SH | $CH_3$ | $CH_3$ | 2-pyridinyl | |
| 1.191 | SH | $C_2H_5$ | $CH_3$ | 2-pyridinyl | m.p. 153-155° C. |
| 1.192 | SH | $C_3H_7\text{-}n$ | $CH_3$ | $C_6H_5\text{-}$ | m.p. 118.5-121° C. |
| 1.193 | SH | $C_2H_5$ | $CH_3$ | $C_6H_5\text{-}$ | $(+)\text{-}R$ |
| 1.194 | SH | $C_2H_5$ | $CH_3$ | $C_6H_5\text{-}$ | $(-)\text{-}S$ |
| 1.195 | SH | $CH_3$ | H | $4\text{-}CH_3\text{-}C_6H_4\text{-}$ | m.p. 166.9° C. |
| 1.196 | SH | $CH_3$ | H | $4\text{-}CH_3O\text{-}C_6H_4\text{-}$ | m.p. 199° C. |
| 1.197 | SH | $CH_3$ | H | $4\text{-}Cl\text{-}C_6H_4\text{-}$ | m.p. 177.7° C. |
| 1.198 | SH | $C_2H_5$ | $CH_3$ | $4\text{-}F\text{-}C_6H_4\text{-}$ | m.p. 137.8° C. |
| 1.199 | SH | $C_2H_5$ | $CH_3$ | $4\text{-}F\text{-}C_6H_4\text{-}$ | $(+)$ |
| 1.200 | SH | $C_2H_5$ | $CH_3$ | $4\text{-}F\text{-}C_6H_4\text{-}$ | $(-)$ |
| 1.201 | SH | $CH_3$ | $C_3H_7\text{-}n$ | $4\text{-}Cl\text{-}C_6H_4\text{-}$ | m.p. 213.1° C. |
| 1.202 | SH | $CH_3$ | $C_3H_7\text{-}n$ | $4\text{-}F\text{-}C_6H_4\text{-}$ | m.p. 200.2° C. |
| 1.203 | SH | $CH_3$ | $C_2H_5$ | $3\text{-}Cl\text{-}4\text{-}Cl\text{-}C_6H_3\text{-}$ | m.p. 166.8° C. |
| 1.204 | SH | $CH_3$ | $C_3H_7\text{-}n$ | $3\text{-}Cl\text{-}C_6H_4\text{-}$ | |
| 1.205 | SH | $CH_3$ | $C_3H_7\text{-}n$ | $3\text{-}Cl\text{-}4\text{-}Cl\text{-}C_6H_3\text{-}$ | |
| 1.206 | SH | $CH_3$ | $C_3H_7\text{-}n$ | $2\text{-}Cl\text{-}C_6H_4\text{-}$ | |
| 1.207 | SH | $CH_3$ | $C_3H_7\text{-}n$ | $2\text{-}Cl\text{-}5\text{-}Cl\text{-}C_6H_3\text{-}$ | |
| 1.208 | SH | $CH_3$ | 2-pyridinyl | $C_6H_5\text{-}$ | |
| 1.209 | H | H | 2-pyridinyl | $C_6H_5\text{-}$ | |
| 1.210 | SH | $CH_3$ | 1-naphthalenyl | $C_6H_5\text{-}$ | |
| 1.211 | H | H | 1-naphthalenyl | $C_6H_5\text{-}$ | |
| 1.212 | SH | $C_2H_5$ | $CH_3$ | $2\text{-}Br\text{-}C_6H_4\text{-}$ | R-form |
| 1.213 | SH | $CH_3$ | 4-pyridinyl | $C_6H_5\text{-}$ | |
| 1.214 | H | H | 4-pyridinyl | $C_6H_5\text{-}$ | |
| 1.215 | SH | $CH_3$ | 3-pyridinyl | $C_6H_5\text{-}$ | |
| 1.216 | H | H | 3-pyridinyl | $C_6H_5\text{-}$ | |
| 1.217 | H | $CH_3$ | $C_3H_7\text{-}n$ | $3\text{-}Cl\text{-}C_6H_4\text{-}$ | resin |
| 1.218 | H | $CH_3$ | cyclohexyl | $C_6H_5\text{-}$ | $.HNO_3$/m.p. 169.0° C. |
| 1.219 | H | $CH_3$ | $C_3H_7\text{-}n$ | 3-pyridinyl | |
| 1.220 | SH | $CH_3$ | $C_3H_7\text{-}n$ | 3-pyridinyl | |
| 1.221 | H | H | $C_3H_7\text{-}n$ | $4\text{-}F\text{-}C_6H_4\text{-}$ | m.p. 126.9° C. |
| 1.222 | H | H | $C_3H_7\text{-}n$ | $2\text{-}Cl\text{-}C_6H_4\text{-}$ | m.p. 183.6° C. |
| 1.223 | SH | $CH_3$ | $C_2H_5$ | $2\text{-}Cl\text{-}C_6H_4\text{-}$ | |
| 1.224 | H | $CH_3$ | $C_2H_5$ | $2\text{-}Cl\text{-}C_6H_4\text{-}$ | |
| 1.225 | H | H | $C_2H_5$ | $2\text{-}Cl\text{-}C_6H_4\text{-}$ | |
| 1.226 | SH | $CH_3$ | $C_3H_7\text{-}i$ | $2\text{-}Cl\text{-}C_6H_4\text{-}$ | |
| 1.227 | H | $CH_3$ | $C_3H_7\text{-}i$ | $2\text{-}Cl\text{-}C_6H_4\text{-}$ | |
| 1.228 | H | H | $C_3H_7\text{-}i$ | $2\text{-}Cl\text{-}C_6H_4\text{-}$ | |
| 1.229 | SH | $CH_3$ | $C_4H_9\text{-}n$ | $2\text{-}Cl\text{-}C_6H_4\text{-}$ | |
| 1.230 | H | $CH_3$ | $C_4H_9\text{-}n$ | $2\text{-}Cl\text{-}C_6H_4\text{-}$ | |
| 1.231 | H | H | $C_4H_9\text{-}n$ | $2\text{-}Cl\text{-}C_6H_4\text{-}$ | |
| 1.232 | H | H | $C_3H_7\text{-}n$ | $3\text{-}Cl\text{-}C_6H_4\text{-}$ | |
| 1.233 | H | H | $C_3H_7\text{-}n$ | $2\text{-}CH_3\text{-}C_6H_4\text{-}$ | |
| 1.234 | H | H | $C_3H_7\text{-}n$ | $2\text{-}OCH_3\text{-}C_6H_4\text{-}$ | |

TABLE 1-continued

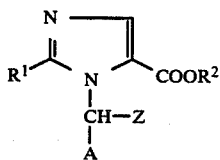

| Comp. No. | R¹ | R² | A | Z | physical data |
|---|---|---|---|---|---|
| 1.235 | SH | CH₃ | C₄H₉—i | C₆H₅— | |
| 1.236 | H | CH₃ | C₄H₉—i | C₆H₅— | |
| 1.237 | SH | CH₃ | 2-CH₃—cyclohexyl | C₆H₅— | |
| 1.238 | H | CH₃ | 2-CH₃—cyclohexyl | C₆H₅— | |
| 1.239 | SH | CH₃ | benzyl | C₆H₅— | m.p. 187.9° C. |
| 1.240 | H | CH₃ | benzyl | C₆H₅— | .HNO₃/m.p. 170.9° C. |
| 1.241 | H | CH₃ | benzyl | C₆H₅— | m.p. 73–74° C. |
| 1.242 | H | H | benzyl | C₆H₅— | m.p. 226.4° C. |
| 1.243 | SH | CH₃ | CH₃—O—CH₂— | C₆H₅— | m.p. 201–202° C. |
| 1.244 | H | CH₃ | CH₃—O—CH₂— | C₆H₅— | resin |
| 1.245 | SH | CH₃ | C₆H₅(CH₂)₂— | C₆H₅— | resin |
| 1.246 | H | CH₃ | C₆H₅(CH₂)₂— | C₆H₅— | .HNO₃/m.p. 141.3° C. |
| 1.247 | SH | CH₃ | C₂H₅—O—CH(C₆H₅)— | C₆H₅— | |
| 1.248 | H | CH₃ | C₂H₅—O—CH(C₆H₅)— | C₆H₅— | .HNO₃/m.p. 160.2° C. |
| 1.249 | H | H | C₂H₅—O—CH(C₆H₅)— | C₆H₅— | |
| 1.250 | H | H | C₃H₇—n | C₆H₅— | m.p. 68.3° C. |
| 1.251 | H | H | cyclohexyl | C₆H₅— | m.p. 249.5° C. |
| 1.252 | H | H | 2-pyridinyl | C₆H₅— | m.p. 214.5° C. |
| 1.253 | H | CH₃ | 2-pyridinyl | C₆H₅— | m.p. 96.3° C. |
| 1.254 | H | C₃H₇—i | 2-pyridinyl | C₆H₅— | m.p. 127.7° C. |
| 1.255 | H | cylohexyl | 2-pyridinyl | C₆H₅— | m.p. 161.0° C. |
| 1.256 | H | CH₃OC₂H₄ | CH₃ | C₆H₅— | .HCl/m.p. 112–114° C. |
| 1.257 | SH | CH₃OC₂H₄ | CH₃ | C₆H₅— | |
| 1.258 | H | C₆H₅—CH₂ | CH₃ | C₆H₅— | .HCl/m.p. 145.5–148° C. |
| 1.259 | SH | C₆H₅—CH₂ | CH₃ | C₆H₅— | |
| 1.260 | SH | CH₃ | C₃H₇—n | 2-pyridinyl | crystals |
| 1.261 | H | CH₃ | C₃H₇—n | 2-pyridinyl | solid residue |
| 1.262 | H | H | C₃H₇—n | 2-pyridinyl | |
| 1.263 | SH | CH₃ | C₃H₇—n | 4-pyridinyl | crystals |
| 1.264 | H | CH₃ | C₃H₇—n | 4-pyridinyl | solid residue |
| 1.265 | H | H | C₃H₇—n | 4-pyridinyl | |
| 1.266 | SH | CH₃ | C₄H₉—n | 3-pyridinyl | m.p. 180.2° C. |
| 1.267 | H | CH₃ | C₄H₉—n | 3-pyridinyl | oil |
| 1.268 | H | H | C₄H₉—n | 3-pyridinyl | |
| 1.269 | SH | CH₃ | cyclopropyl | C₆H₅— | crystals |
| 1.270 | H | CH₃ | cyclopropyl | C₆H₅— | .HNO₃/m.p. 118.3° C. |
| 1.271 | H | H | cyclopropyl | C₆H₅— | |
| 1.272 | HS | CH₃ | cyclopentyl | C₆H₅— | |
| 1.273 | H | CH₃ | cyclopentyl | C₆H₅— | |
| 1.274 | H | H | cyclopentyl | C₆H₅— | |
| 1.275 | HS | CH₃ | 1-methylcyclopentyl | C₆H₅— | |
| 1.276 | H | CH₃ | 1-methylcyclopentyl | C₆H₅— | |
| 1.277 | H | H | 1-methylcyclopentyl | C₆H₅— | |
| 1.278 | SH | CH₃ | C₅H₁₁—n | C₆H₅— | |
| 1.279 | H | CH₃ | C₅H₁₁—n | C₆H₅— | |
| 1.280 | SH | CH₃ | C₆H₁₃—n | C₆H₅— | |
| 1.281 | H | CH₃ | C₆H₁₃—n | C₆H₅— | |
| 1.282 | SH | CH₃ | C₇H₁₅—n | C₆H₅— | |
| 1.283 | H | CH₃ | C₇H₁₅—n | C₆H₅— | |
| 1.284 | H | H | C₃H₇—n | 4-Cl—C₆H₄— | |
| 1.285 | SH | CH₃ | C₃H₇—n | 2-F—C₆H₄— | |
| 1.286 | H | CH₃ | C₃H₇—n | 2-F—C₆H₄— | |
| 1.287 | H | H | C₃H₇—n | 2-F—C₆H₄— | |
| 1.288 | SH | CH₃ | C₃H₇—n | 3-F—C₆H₄— | |
| 1.289 | H | CH₃ | C₃H₇—n | 3-F—C₆H₄— | |
| 1.290 | H | H | C₃H₇—n | 3-F—C₆H₄— | |
| 1.291 | SH | CH₃ | C₃H₇—n | 2-Br—C₆H₄— | |
| 1.292 | H | CH₃ | C₃H₇—n | 2-Br—C₆H₄— | |
| 1.293 | H | H | C₃H₇—n | 2-Br—C₆H₄— | |
| 1.294 | SH | CH₃ | C₃H₇—n | 3-Br—C₆H₄— | |
| 1.295 | H | CH₃ | C₃H₇—n | 3-Br—C₆H₄— | |
| 1.296 | H | H | C₃H₇—n | 3-Br—C₆H₄— | |
| 1.297 | SH | CH₃ | C₃H₇—n | 4-Br—C₆H₄— | |
| 1.298 | H | CH₃ | C₃H₇—n | 4-Br—C₆H₄— | |
| 1.299 | H | H | C₃H₇—n | 4-Br—C₆H₄— | |
| 1.300 | H | H | C₃H₇—n | 2-Cl—4-Cl—C₆H₃— | |
| 1.301 | H | H | C₃H₇—n | 3-Cl—4-Cl—C₆H₃— | |
| 1.302 | SH | CH₃ | C₃H₇—n | 2-CN—C₆H₄— | |
| 1.303 | H | CH₃ | C₃H₇—n | 2-CN—C₆H₄— | |
| 1.304 | H | H | C₃H₇—n | 2-CN—C₆H₄— | |
| 1.305 | SH | CH₃ | C₃H₇—n | 2-NO₂—C₆H₄— | |

TABLE 1-continued

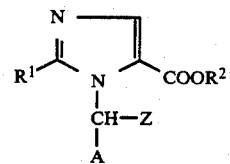

| Comp. No. | $R^1$ | $R^2$ | A | Z | physical data |
|---|---|---|---|---|---|
| 1.306 | H | $CH_3$ | $C_3H_7-n$ | $2\text{-}NO_2\text{-}C_6H_4-$ | |
| 1.307 | H | H | $C_3H_7-n$ | $2\text{-}NO_2\text{-}C_6H_4-$ | |
| 1.308 | SH | $CH_3$ | (2-pyridinyl)methyl | $C_6H_5$ | .HCl/m.p. 200° C. |
| 1.309 | H | $CH_3$ | (2-pyridinyl)methyl | $C_6H_5$ | |
| 1.310 | H | H | (2-pyridinyl)methyl | $C_6H_5$ | .2 HCl/m.p. 179.6° C. |
| 1.311 | SH | $CH_3$ | (2-thienyl)methyl | $C_6H_5$ | |
| 1.312 | H | $CH_3$ | (2-thienyl)methyl | $C_6H_5$ | |
| 1.313 | H | H | (2-thienyl)methyl | $C_6H_5$ | |
| 1.314 | SH | $CH_3$ | (2-furanyl)methyl | $C_6H_5$ | |
| 1.315 | H | $CH_3$ | (2-furanyl)methyl | $C_6H_5$ | |
| 1.316 | H | H | (2-furanyl)methyl | $C_6H_5$ | |
| 1.317 | SH | $CH_3$ | (2-pyrimidinyl)methyl | $C_6H_5$ | |
| 1.318 | H | $CH_3$ | (2-pyrimidinyl)methyl | $C_6H_5$ | |
| 1.319 | H | H | (2-pyrimidinyl)methyl | $C_6H_5$ | |
| 1.320 | H | $CH_3$ | 1-naphthalenyl | 1-naphthalenyl | .$HNO_3$/m.p. 220° C. |
| 1.321 | SH | $CH_3$ | 1-naphthalenyl | 1-naphthalenyl | |
| 1.322 | H | H | 1-naphthalenyl | 1-naphthalenyl | |
| 1.323 | SH | $CH_3$ | 2-naphthalenyl | 2-naphthalenyl | |
| 1.324 | H | $CH_3$ | 2-naphthalenyl | 2-naphthalenyl | |
| 1.325 | SH | $CH_3$ | $CH_3$ | 2-thienyl | m.p. 162–164° C. |
| 1.326 | H | $CH_3$ | $CH_3$ | 2-thienyl | m.p. 135.5–138° C. |
| 1.327 | H | $CH_3$ | H | 2-thienyl | m.p. 192° C. |
| 1.328 | H | $C_6H_5\text{-}CH(CH_3)$ | $CH_3$ | $C_6H_5-$ | |

TABLE 2

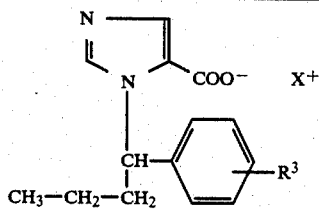

| Comp. No. | $R^3$ | $X^+$ | physical data |
|---|---|---|---|
| 2.01 | 2-Cl | $^+NH_2(CH_3)_2$ | |
| 2.02 | 2-Cl | $^+NH_3\text{-}CH_3$ | |
| 2.03 | 2-Cl | $^+NH_2(C_2H_5)_2$ | |
| 2.04 | 2-Cl | $^+NH_2(C_3H_7\text{-}i)_2$ | |
| 2.05 | 2-Cl | $^+NH_2(CH_2\text{-}CH_2OH)_2$ | |
| 2.06 | 2-Cl | $^+NH_4$ | |
| 2.07 | 2-Cl | $^+NH_3\text{-}CH_2\text{-}CH_2OH$ | |
| 2.08 | 2-Cl | piperidinium ($H_2\overset{+}{N}$) | |
| 2.09 | 2-Cl | morpholinium ($H_2\overset{+}{N}\text{-}O$) | |
| 2.10 | 2-Cl | 2,6-dimethylmorpholinium | |

TABLE 2-continued

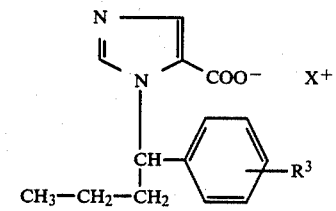

| Comp. No. | $R^3$ | $X^+$ | physical data |
|---|---|---|---|
| 2.11 | 2-Cl | $^+NH_3\text{-}CH_2\text{-}COOC_2H_5$ | |
| 2.12 | 2-Cl | $H_3C\text{-}^+NH_2\text{-}CH_2\text{-}COOC_2H_5$ | |
| 2.13 | 2-Cl | $^+NH_3\text{-}CH_2\text{-}(2\text{-}Cl\text{-}C_6H_4)$ | |
| 2.14 | 2-Cl | $K^+$ | .$2H_2O$/m.p. 70.7° C. |
| 2.15 | 2-Cl | $Na^+$ | |
| 2.16 | 2-Cl | $\frac{1}{2}Ca^{2+}$ | |
| 2.17 | 2-Cl | $^+N(CH_3)_3\text{-}CH_2\text{-}CH_2Cl$ | |
| 2.18 | 2-Cl | $(CH_3)_2\overset{+}{N}$ (piperidinium) | |
| 2.19 | 2-Cl | $(CH_3)_2\overset{+}{N}\text{-}O$ (morpholinium) | |

TABLE 2-continued

Structure: imidazole with N-CH(CH2-CH3)-phenyl-R³ substituent, COO⁻ X⁺

| Comp. No. | R³ | X⁺ | physical data |
|---|---|---|---|
| 2.20 | 2-Cl | ⁺NH₃—CH₂—(4-Cl-C₆H₄) | |
| 2.21 | 2-CH₃ | ⁺NH₂(CH₃)₂ | |
| 2.22 | 2-CH₃ | ⁺NH₃—CH₃ | |
| 2.23 | 2-CH₃ | ⁺NH₂(C₂H₅)₂ | |
| 2.24 | 2-CH₃ | ⁺NH₂(C₃H₇—i)₂ | |
| 2.25 | 2-CH₃ | ⁺NH₂(CH₂—CH₂OH)₂ | |
| 2.26 | 2-CH₃ | ⁺NH₄ | |
| 2.27 | 2-CH₃ | ⁺NH₃—CH₂—CH₂OH | |
| 2.28 | 2-CH₃ | piperidinium (H₂N⁺) | |
| 2.29 | 2-CH₃ | morpholinium (H₂N⁺—O) | |
| 2.30 | 2-CH₃ | 2,6-dimethylmorpholinium (H₂N⁺, CH₃) | |
| 2.31 | 2-CH₃ | ⁺NH₃—CH₂—COOC₂H₅ | |
| 2.32 | 2-CH₃ | H₃C—⁺NH₂—CH₂—COOC₂H₅ | |
| 2.33 | 2-CH₃ | ⁺NH₃—CH₂—(2-Cl-C₆H₄) | |
| 2.34 | 2-CH₃ | K⁺ | |
| 2.35 | 2-CH₃ | Na⁺ | |
| 2.36 | 2-CH₃ | ½Ca²⁺ | |
| 2.37 | 2-CH₃ | ⁺N(CH₃)₃—CH₂—CH₂Cl | |
| 2.38 | 2-CH₃ | N,N-dimethylpiperidinium ((CH₃)₂N⁺) | |
| 2.39 | 2-CH₃ | N,N-dimethylmorpholinium ((CH₃)₂N⁺—O) | |
| 2.40 | 2-CH₃ | ⁺NH₃—CH₂—(4-Cl-C₆H₄) | |
| 2.41 | 3-Cl | ⁺NH₂(CH₃)₂ | |
| 2.42 | 3-Cl | ⁺NH₃—CH₃ | |
| 2.43 | 3-Cl | ⁺NH₂(C₂H₅)₂ | |
| 2.44 | 3-Cl | ⁺NH₂(C₃H₇—i)₂ | |
| 2.45 | 3-Cl | ⁺NH₂(CH₂—CH₂OH)₂ | |
| 2.46 | 3-Cl | ⁺NH₄ | |
| 2.47 | 3-Cl | ⁺NH₃—CH₂—CH₂OH | |
| 2.48 | 3-Cl | piperidinium (H₂N⁺) | |
| 2.49 | 3-Cl | morpholinium (H₂N⁺—O) | |
| 2.50 | 3-Cl | 2,6-dimethylmorpholinium (H₂N⁺, CH₃) | |
| 2.51 | 3-Cl | ⁺NH₃—CH₂—COOC₂H₅ | |
| 2.52 | 3-Cl | H₃C—⁺NH₂—CH₂—COOC₂H₅ | |
| 2.53 | 3-Cl | ⁺NH₃—CH₂—(2-Cl-C₆H₄) | |
| 2.54 | 3-Cl | K⁺ | |
| 2.55 | 3-Cl | Na⁺ | |
| 2.56 | 3-Cl | ½Ca²⁺ | |
| 2.57 | 3-Cl | ⁺N(CH₃)₃—CH₂—CH₂Cl | |
| 2.58 | 3-Cl | N,N-dimethylpiperidinium ((CH₃)₂N⁺) | |
| 2.59 | 3-Cl | N,N-dimethylmorpholinium ((CH₃)₂N⁺—O) | |
| 2.60 | 3-Cl | ⁺NH₃—CH₂—(4-Cl-C₆H₄) | |
| 2.61 | 2-OCH₃ | ⁺NH₂(CH₃)₂ | |
| 2.62 | 2-OCH₃ | ⁺NH₃—CH₃ | |
| 2.63 | 2-OCH₃ | ⁺NH₂(C₂H₅)₂ | |
| 2.64 | 2-OCH₃ | ⁺NH₂(C₃H₇—i)₂ | |
| 2.65 | 2-OCH₃ | ⁺NH₂(CH₂—CH₂OH)₂ | |

TABLE 2-continued

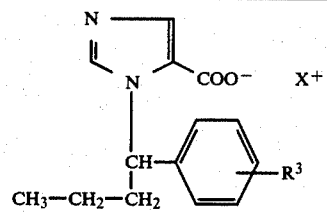

| Comp. No. | R³ | X⁺ | physical data |
|---|---|---|---|
| 2.66 | 2-OCH₃ | ⁺NH₄ | |
| 2.67 | 2-OCH₃ | ⁺NH₃—CH₂—CH₂OH | |
| 2.68 | 2-OCH₃ | H₂N⁺(pyrrolidinium) | |
| 2.69 | 2-OCH₃ | H₂N⁺(morpholinium) | |
| 2.70 | 2-OCH₃ | H₂N⁺(2,6-dimethylmorpholinium) | |
| 2.71 | 2-OCH₃ | ⁺NH₃—CH₂—COOC₂H₅ | |
| 2.72 | 2-OCH₃ | H₃C—⁺NH₂—CH₂—COOC₂H₅ | |

TABLE 2-continued

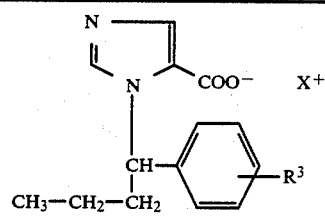

| Comp. No. | R³ | X⁺ | physical data |
|---|---|---|---|
| 2.73 | 2-OCH₃ | ⁺NH₃—CH₂—(2-Cl-C₆H₄) | |
| 2.74 | 2-OCH₃ | K⁺ | |
| 2.75 | 2-OCH₃ | Na⁺ | |
| 2.76 | 2-OCH₃ | ½Ca²⁺ | |
| 2.77 | 2-OCH₃ | ⁺N(CH₃)₃—CH₂—CH₂Cl | |
| 2.78 | 2-OCH₃ | (CH₃)₂N⁺(piperidinium) | |
| 2.79 | 2-OCH₃ | (CH₃)₂N⁺(morpholinium) | |
| 2.80 | 2-OCH₃ | ⁺NH₃—CH₂—(4-Cl-C₆H₄) | |

TABLE 3

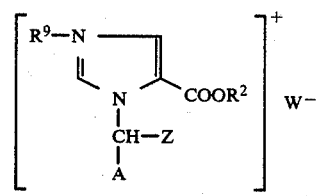

| Comp. No. | R² | A | Z | R⁹ | W | physical data |
|---|---|---|---|---|---|---|
| 3.01 | CH₃ | CH₃ | C₆H₅ | CH₃ | I | mp. 123.5–125° C. |
| 3.02 | CH₃ | C₃H₇—n | C₆H₅ | CH₃ | I | |
| 3.03 | CH₃ | C₃H₇—n | 2-Cl—C₆H₄ | CH₃ | I | |
| 3.04 | CH₃ | C₃H₇—n | 3-Cl—C₆H₄ | CH₃ | I | |
| 3.05 | CH₃ | C₃H₇—n | 2-CH₃—C₆H₄ | CH₃ | I | |
| 3.06 | CH₃ | C₃H₇—n | 3-CH₃—C₆H₄ | CH₃ | I | |
| 3.07 | CH₃ | C₃H₇—n | 4-CH₃—C₆H₄ | CH₃ | I | |
| 3.08 | CH₃ | C₃H₇—n | 2-CH₃O—C₆H₄ | CH₃ | I | |
| 3.09 | CH₃ | C₃H₇—n | 3-CH₃O—C₆H₄ | CH₃ | I | |
| 3.10 | CH₃ | C₃H₇—n | 3-CF₃—C₆H₄ | CH₃ | I | |
| 3.11 | CH₃ | C₃H₇—n | 3-F—C₆H₄ | CH₃ | I | |
| 3.12 | CH₃ | C₃H₇—n | C₆H₅ | CH₂—C₆H₅ | Br | |
| 3.13 | CH₃ | C₃H₇—n | C₆H₅ | CH₂—C₆H₅ | Cl | |
| 3.14 | CH₃ | C₃H₇—n | 2-Cl—C₆H₄ | CH₂—C₆H₅ | Br | |
| 3.15 | CH₃ | C₃H₇—n | 3-Cl—C₆H₄ | CH₂—C₆H₅ | Br | |
| 3.16 | CH₃ | C₃H₇—n | 2-CH₃—C₆H₄ | CH₂—C₆H₅ | Br | |
| 3.17 | CH₃ | C₃H₇—n | 2-CH₃O—C₆H₄ | CH₂—C₆H₅ | Br | |
| 3.18 | CH₃ | C₃H₇—n | C₆H₅ | C₂H₅ | I | |
| 3.19 | CH₃ | C₃H₇—n | 2-Cl—C₆H₄ | C₂H₅ | I | |
| 3.20 | CH₃ | C₃H₇—n | C₆H₅ | C₃H₇—n | Br | |
| 3.21 | CH₃ | C₃H₇—n | 2-Cl—C₆H₄ | C₃H₇—n | Br | |
| 3.22 | CH₃ | C₃H₇—n | C₆H₅ | C₄H₉—n | Br | |
| 3.23 | CH₃ | C₃H₇—n | 2-Cl—C₆H₄ | C₄H₉—n | Br | |

TABLE 3-continued

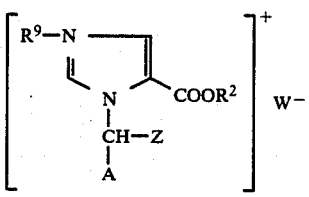

| Comp. No. | R² | A | Z | R⁹ | W | physical data |
|---|---|---|---|---|---|---|
| 3.24 | CH₃ | C₃H₇—n | C₆H₅ | CH₂COC₆H₅ | Br | |
| 3.25 | CH₃ | C₃H₇—n | 2-Cl—C₆H₄ | CH₂COC₆H₅ | Br | |
| 3.26 | CH₃ | C₃H₇—n | C₆H₅ | CH₂CO—2,4-(Cl)₂—C₆H₃ | Br | |
| 3.27 | CH₃ | C₃H₇—n | 2-Cl—C₆H₄ | CH₂CO—2,4-(Cl)₂—C₆H₃ | Br | |
| 3.28 | CH₃ | C₃H₇—n | C₆H₅ | CH₂—CH=CH₂ | Br | |
| 3.29 | CH₃ | C₃H₇—n | 2-Cl—C₆H₄ | CH₂—CH=CH₂ | Br | |
| 3.30 | C₂H₅ | CH₃ | C₆H₅ | CH₃ | I | (−) mp. 159.5° C. |
| 3.31 | C₂H₅ | C₃H₇—n | C₆H₅ | CH₃ | I | |
| 3.32 | C₂H₅ | C₃H₇—n | 2-Cl—C₆H₄ | CH₃ | I | |
| 3.33 | C₂H₅ | C₃H₇—n | 2-CH₃—C₆H₄ | CH₃ | I | |
| 3.34 | C₂H₅ | C₃H₇—n | 2-CH₃O—C₆H₄ | CH₃ | I | |

TABLE 4

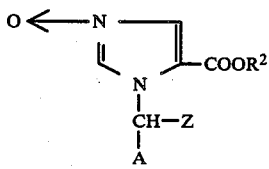

| Comp. No. | R² | A | Z | physical data |
|---|---|---|---|---|
| 4.01 | CH₃ | C₃H₇—n | C₆H₅ | |
| 4.02 | CH₃ | C₃H₇—n | 2-Cl—C₆H₄ | |
| 4.03 | CH₃ | C₃H₇—n | 3-Cl—C₆H₄ | |
| 4.04 | CH₃ | C₃H₇—n | 2-CH₃—C₆H₄ | |
| 4.05 | CH₃ | C₃H₇—n | 4-CH₃—C₆H₄ | |
| 4.06 | CH₃ | C₃H₇—n | 2-CH₃O—C₆H₄ | |
| 4.07 | CH₃ | C₃H₇—n | 3-CH₃O—C₆H₄ | |
| 4.08 | CH₃ | C₃H₇—n | 3-CF₃—C₆H₄ | |
| 4.09 | CH₃ | C₃H₇—n | 2-F—C₆H₄ | |
| 4.10 | C₂H₅ | C₃H₇—n | C₆H₅ | |
| 4.11 | C₂H₅ | C₃H₇—n | 2-Cl—C₆H₄ | |
| 4.12 | C₂H₅ | C₃H₇—n | 2-CH₃—C₆H₄ | |
| 4.13 | C₂H₅ | C₃H₇—n | 2-CH₃O—C₆H₄ | |

The following examples are intended to illustrate the present invention in all its aspects and not to limit it thereto.

A. COMPOSITION EXAMPLES

Example 1:

Composition examples for solid compounds of formula (I) (percentages are by weight)

| (a) Wettable powders | (a) | (b) | (c) |
|---|---|---|---|
| compound of formula (I) | 20% | 50% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7-8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient was thoroughly mixed with the adjuvants and the mixture was thoroughly ground in a suitable mill, affording wettable powders which could be diluted with water to give suspensions of the desired concentration.

| (b) Emulsifiable concentrate | (a) | (b) |
|---|---|---|
| compound of formula (I) | 10% | 1% |
| octylphenol polyethylene glycol ether (4-5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| dimethylbenzene mixture | 50% | 79% |

Emulsions of any required concentration could be obtained from this concentrate by dilution with water.

| (c) Dusts | (a) | (b) |
|---|---|---|
| compound of formula (I) | 0.1% | 1% |
| talcum | 99.9% | — |
| kaolin | — | 99% |

Usable dusts were obtained by mixing the active ingredient with the carriers, and grinding the mixture in a suitable mill.

| (d) Extruder granulate | (a) | (b) |
|---|---|---|
| compound of formula (I) | 10% | 1% |
| sodium lignosulfate | 2% | 2% |
| carboxymethylcellulose | 1% | 1% |
| kaolin | 87% | 96% |

The active ingredient was mixed and ground with the adjuvants, and the mixture was subsequently moistened with water. The mixture was extruded and dried in a stream of air.

| (e) Coated granulate | |
|---|---|
| compound of formula (I) | 3% |
| polyethylene glycol (mol. wt. 200) | 2% |

| (e) Coated granulate | |
|---|---|
| kaolin | 94% |

The finely ground active ingredient was uniformly applied, in a mixer, to the kaolin moistened with polyethylene glycol. Non-dusty coated granulates were obtained in this manner.

| (f) Suspension concentrate | (a) | (b) |
|---|---|---|
| compound of formula (I) | 40% | 5% |
| ethylene glycol | 10% | 10% |
| nonylphenol polyethylene glycol ether (15 moles of ethylene oxide) | 6% | 1% |
| sodium lignosulfate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient was intimately mixed with the adjuvants, giving a suspension concentrate from which suspension of any desired concentration could be obtained by dilution with water.

| (g) Salt solution | |
|---|---|
| compound of formula (I) | 5% |
| isopropylamine | 1% |
| octylphenol polyethylene glycol ether (78 moles of ethylene oxide) | 3% |
| water | 91 |

Example 2:

Composition examples for liquid active ingredients of formula (I) (throughout, percentages are by weight)

| (a) Emulsifiable concentrates | (a) | (b) | (c) |
|---|---|---|---|
| compound of formula (I) | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| dimethylbenzene mixture | 70% | 25% | 20% |

Emulsions of any required concentration could be produced from such concentrate by dilution with water.

| (b) Solutions | (a) | (b) | (c) | (d) |
|---|---|---|---|---|
| compound of formula (I) | 80% | 10% | 5% | 95% |
| ethylene glycol monoethyl ether | 20% | — | — | — |
| polyethylene glycol (MG 400) | — | 70% | — | — |
| N—methyl-2-pyrrolidone | — | 20% | — | — |
| epoxidised coconut oil | — | — | 1% | 5% |
| petroleum distillate (boiling range 160–190° C.) | — | — | 94% | — |

These solutions were suitable for application in the form of microdrops.

| (c) Granulates | (a) | (b) |
|---|---|---|
| compound of formula (I) | 5% | 10% |
| kaolin | 94% | — |
| highly dispersed silicic acid | 1% | — |
| attapulgite | — | 90% |

The active ingredient was dissolved in methylene chloride, the solution was sprayed onto the carrier, and the solvent was subsequently evaporated off in vacuo.

| (d) Dusts | (a) | (b) |
|---|---|---|
| compound of formula (I) | 2% | 5% |
| highly dispersed silicic acid | 1% | 5% |
| talcum | 97% | — |
| kaolin | — | 90% |

Ready-for-use dusts were obtained by intimately mixing the carriers with the active ingredient.

B. BIOLOGICAL EXAMPLES

Example 3:

Preemergence herbicidal action

In a greenhouse, immediately after sowing the test plants in seed dishes, the surface of the soil was treated with an aqueous dispersion of the test compounds, obtained from a 25% emulsifiable concentrate or from a 25% wettable powder with test compounds, which, on account of their insufficient solubility, could not be formulated to emulsifiable concentrates. Two different concentration series were used, corresponding to 2 and 1 kg of test compound per hectare respectively. The seed dishes were kept in the greenhouse at 22°–25° C. and 50–70% relative humidity. The test was evaluated 3 weeks later in accordance with the following rating:

1 = plants had not germinated or were totally withered
2–3 = very strong action
4–6 = average action
7–8 = slight action
9 = no action In this test, the tested compounds of formula (I) were most effective against monocotyledonous grass weeds, whereas no or only insignificant damage was caused to cultivated plants such as maize at the given rates of application.

Results: Preemergence test
—: not tested

| | dosage kg a.i./ha | | | | | |
|---|---|---|---|---|---|---|
| | Comp. 1.18 | | Comp. 1.21 | | Comp. 1.27 | |
| plant tested | 2 | 1 | 2 | 1 | 2 | 1 |
| maize | 9 | 9 | 9 | 9 | 9 | 9 |
| alopecurus myos. | 2 | 4 | 5 | 7 | 5 | 7 |
| digitaria sang. | 1 | 1 | — | — | 1 | 1 |
| echinochloa c.g. | 6 | 9 | 2 | 6 | 3 | 9 |
| sida spinosa | 4 | 5 | — | — | 4 | 4 |
| amaranthus ret. | 2 | 3 | — | — | 1 | 2 |
| chenopodium sp. | 2 | 3 | 2 | 2 | 1 | 2 |
| solanum nigrum | 4 | 4 | — | — | 2 | 3 |
| chrysanthe. leuc. | 2 | 2 | — | — | 2 | 3 |
| galium aparine | 2 | 2 | 3 | 3 | 4 | 6 |
| viola tricolor | 1 | 2 | 1 | 2 | 4 | 5 |
| veronia sp. | 1 | 2 | — | — | 2 | 3 |

Example 4:

Postemergence herbicidal action (Contact herbicide)

A large number of weeds and cultivated plants were sprayed postemergence in the 4- to 6-leaf stage with an aqueous active ingredient dispersion in rates of 4 to 2 kg of test compound per hectare and kept at 24°-26° C. and 45-60% relative humidity. The test was evaluated at least 15 days after treatment in accordance with the same rating as employed in the preemergence test.

In this test, the compounds of formula (I) were also most effective against the tested weeds. The cultivated plants such as maize and rice were either not damaged or only damaged at higher application rates of the tested compound.

Results: Postemergence test

| plant tested | dosage g.a.i./ha Comp. 1.27 | |
|---|---|---|
| | 4000 | 2000 |
| maize | 8 | 9 |
| rice, dry | 8 | 9 |
| xanthium sp. | 3 | 4 |
| chenopodium sp. | 5 | 6 |
| ipomoena | 3 | 4 |
| sinapis | 3 | 4 |
| galium aparine | 4 | 5 |
| viola tricolor | 3 | 3 |

Example 5:

Herbicidal action in transplanted rice crops 25 days old rice shoots of the variety "Yamabiko" were transplanted into large plastic containers. Into the same containers seeds of the weeds occuring in rice crops, namely ammonia, cyperus, echinochloa and rotala, were sown between the rice plants. The containers were watered to such an extent, that a water layer of 2.5 cm covered the surface. After 3 days under green house conditions, the diluted aqueous dispersions of the active compounds were added to the water layer at a rate of application of 2000, 1000, 500, 250 and 125 g a.i. per hectare. The containers were then kept covered with water at a temperature 25° C. and high humidity in a greenhouse for 4 weeks. The evaluation of the tests was made in accordance with the rating given in Example 3.

Results:

| | Compound No. | | | | | | | | | |
|---|---|---|---|---|---|---|---|---|---|---|
| | 1.21 in g.a. per hectare | | | | | 1.35 in g.a. per hectare | | | | |
| Tested plant | 2000 | 1000 | 500 | 250 | 125 | 2000 | 1000 | 500 | 250 | 125 |
| rice "Yamabiko" | 7 | 7 | 8 | 8 | 8 | 7 | 8 | 8 | 9 | 9 |
| ammonia | 1 | 1 | 1 | 1 | 1 | 1 | 1 | 1 | 2 | 3 |
| cyperus | 1 | 1 | 1 | 1 | 1 | 1 | 1 | 1 | 1 | 2 |
| echinochloa | 1 | 1 | 1 | 4 | 6 | 1 | 2 | 3 | 5 | 6 |
| rotala | 4 | 5 | 6 | 6 | 6 | 4 | 5 | 6 | 8 | 9 |

C. PREPARATORY EXAMPLES

As used throughout the following preparatory examples all parts are by weight.

Example 6

A solution of 1.37 parts of sodium methoxide in 20.5 parts of tetrahydrofuran was prepared by adding the required amounts of methanol and sodium hydride to the tetrahydrofuran. With optional cooling to room temperature 4.1 parts of formic acid methyl ester and 6.0 parts of methyl N-formyl-N-[1-(4-methylphenyl)-butyl]glycine were added. After 20 hours the mixture was taken up in 18 parts of deionisized water and 28 parts of 1,1'-oxybisethane. The aqueous phase was separated, and 14 parts of methanol and 6.5 parts of 36% hydrochloric acid were added. The solution was heated to 40°-45° C. and treated with a solution of 3.7 parts of potassium thiocyanate in 6 parts of deionisized water. After 24 hours the mixture was heated to 80° C. for 5 hours. Upon cooling, the precipitated product was filtered off and dried, yielding 5.23 parts (75%) of methyl 1-1-[1-(4-methylphenyl)butyl]-2-mercapto-1H-imidazole-5-carboxylate; mp. 209°-211° C. (compound 1.41).

Example 7

0.07 Parts of sodium nitrite and 0.6 parts of nitric acid were solved in 2 parts of deionisized water. 1.0 Part of methyl 1-[1-(4-methylphenyl)butyl]-2-mercapto-1H-imidazole-5-carboxylate was added portionwise at a temperature between 25° C. and 30° C. The precipitate was isolated, yielding 0.94 parts (86%) of methyl 1-[1-(4-methylphenyl)butyl]-1H-imidazole-5-carboxylate mononitriate. This colourless salt has a melting point of 141°-143° C. (compound 1.15).

Example 8

A mixture of 44 parts of α-phenyl-2-pyridinemethanamine, 27 parts of methyl chloroacetate, 30 parts of N,N-diethylethanamine and 270 parts of N,N-dimethylformamide was stirred overnight at room temperature. The reaction mixture was poured into 1000 parts of water. The product was extracted with 1,1'-oxybisethane. The extract was washed three times with water, dried, filtered and evaporated, yielding 37 parts (62.8%) of methyl N-[phenyl(2-pyridinyl)methyl]glycine as a residue.

A mixture of 37 parts of methyl N-[phenyl(2-pyridinyl)methyl]glycine, 36 parts of formic acid and 450 parts of dimethylbenzene was stirred and refluxed for 2 hours. The reaction mixture was poured into water. The product was extracted with 1,1'-oxybisethane. The extract was washed successively with a sodium hydroxide solution 10% and water, dried, filtered and evaporated. The residue was purified by column chromatography over silica gel using a mixture of trichloromethane and methanol (90:10 by volume) as eluent. The pure fractions were collected and the eluent was evaporated, yielding 24 parts (60.3%) of methyl N-formyl-N-[phenyl(2-pyridinyl)methyl]glycine as a residue.

To a stirred solution of 2 parts of a sodium hydride dispersion 50% in 45 parts of tetrahydrofuran were added 11.5 parts of methyl N-formyl-N-[phenyl(2-pyridinyl)methyl]glycine. After 10 minutes 2 parts of methyl formate were added and stirring was continued overnight. The reaction mixture was concentrated to a volume of about 20 parts. The precipitated product was filtered off and taken up in 100 parts of water and 70 parts of 1,1'-oxybisethane. The whole was stirred for 15 minutes and the layers were separated. The aqueous phase was acidified with 18 parts of concentrated hydrochloric acid and then 5 parts of potassium thiocyanate were added. Upon stirring over weekend, the product was filtered off and dried, yielding 10.8 parts (83.0%) of methyl 2-mercapto-1-[phenyl(2-pyridinyl)methyl]-1H-imidazole-5-carboxylate (compound 1.208).

Example 9

A mixture of 123.6 parts of methyl 2-mercapto-1-[phenyl(2-pyridinyl)methyl]-1H-imidazole-5-carboxylate, 0.2 parts of sodium nitrite, 219 parts of nitric acid and 440 parts of water was stirred for 2 hours at room temperature. The reaction mixture was poured into water and the whole was treated with a sodium hydroxide solution (on an ice bath). The product was extracted with dichloromethane. The extract was dried, filtered and evaporated. The residue was crystallized twice: first from 2-propanone and then from 4-methyl-2-pentanone. The product was filtered off (the filtrates were set aside) and dried in vacuo at 70° C., yielding a first fraction of 37.2 parts (33.3%) of methyl 1-[phenyl(2-pyridinyl)methyl]-1H-imidazole-5-carboxylate; mp. 96.3° C.

The filtrates, which were set aside (see above) were evaporated. The residue was purified by column chromatography over silica gel using a mixture of trichloromethane and methanol (95:5 by volume) as eluent. The pure fractions were collected and the eluent was evaporated, yielding a second fraction of 31 parts (27.8%) of methyl 1-[phenyl(2-pyridinyl)methyl]-1H-imidazole-5-carboxylate as a residue. Total yield: 68.2 parts (61.1%) of methyl 1-[phenyl(2-pyridinyl)methyl]-1H-imidazole-5-carboxylate (compound 1.253).

Example 10

33.0 Parts of ammonium carbonate are added at room temperature to a solution of 16 parts of methyl 2-[(1,2-diphenylethyl)formylamino]-3-oxopropanoate in 260 parts of dimethylbenzene. The mixture is heated to 70° C. for 1 hour and to 120° C. for a further 3 hours. The reaction mixture is gradually evaporated until precipitation of methyl 1-(1,2-diphenylethyl)-1H-imidazol-5-carboxylate; m.p. 73°-74° C. (compound 1.241).

Example 11

A mixture of 17 parts of methyl 2-[(1,2-diphenylethyl)formylamino]-3-oxopropanoate, 65 parts of ammonium acetate and 100 parts of acetic acid are refluxed for 8 hours. 50 Parts of ammonium acetate are added and refluxing is continued for a further 4 hours. The solution is diluted with 300 parts of water and extracted twice, with 85 parts of methylbenzene each time. The organic phases are combined, concentrated and separated by column chromatography over silica gel. Concentration of the eluate yields methyl 1-(1,2-diphenylethyl)-1H-imidazol-5-carboxylate (compound 1.241).

Example 12

A mixture of 17 parts of methyl 2-[(1,2-diphenylethyl)formylamino]-3-oxopropanoate, 50 parts of formamide and 10 parts of hydrochloric acid are heated to 140° C. for 8 hours. After cooling to room temperature, the mixture is extracted with a mixture of 100 parts of water and 70 parts of 1,1'-oxybisethane. The ethereal phase is separated and the aqueous phase is extracted twice with 79 parts of 1,1'-oxybisethane each time. The combined organic phases are dried over sodium sulfate and concentrated to dryness, yielding methyl 1-(1,2-diphenylethyl)-1H-imidazol-5-carboxylate (compound 1.241).

Example 13

A mixture of 8.7 parts of methyl 1-(cyclohexylphenylmethyl)-1H-imidazole-5-carboxylate mononitrate, 9 parts of a sodium hydroxide solution 50% and 45 parts of water was stirred for 1 hour at reflux temperature. 35 Parts of water were added. After cooling, the reaction mixture was neutralized with acetic acid. The product was extracted with 1,1'-oxybisethane. The extract was dried, filtered and evaporated. The residue was crystallized from a mixture of ethanol and acetonitrile. The product was filtered off (the filtrate was set aside) and dried in vacuo at 50° C., yielding a first fraction of 2.1 parts (30.8%) of 1-(cyclohexylphenylmethyl)-1H-imidazole-5-carboxylic acid; mp. 249.5° C. (compound 1.251).

The filtrate, which was set aside (see above) was evaporated, yielding a second fraction of 5 parts (73%) of 1-(cyclohexylphenylmethyl)-1H-imidazole-5-carboxylic acid; mp. 249.5° C. (compound 1.251).

Example 14

A mixture of 7 parts of 1-[phenyl(2-pyridinyl)methyl]-1H-imidazole-5-carboxylic acid, 5.5 parts of concentrated sulfuric acid and 140 parts of cyclohexanol was stirred for 2 days at 100° C. The reaction mixture was evaporated (at an oil pump) and the residue was taken up in dichloromethane. The organic layer was washed with a sodium hydroxide solution, dried, filtered and evaporated. The residue was purified by column chromatography over silica gel using a mixture of trichloromethane and methanol (90:10 by volume) as eluent. The pure fractions were collected and the eluent was evaporated. The residue was crystallized from acetonitrile. The product was filtered off and dried in vacuo at 60° C., yielding 2.6 parts (28.8%) of cyclohexyl 1-[phenyl(2-pyridinyl)methyl]-1H-imidazole-5-carboxylate; mp. 161.0° C. (compound 1.255).

Example 15

A mixture of 4.6 parts of 1-(1 phenylethyl)-1H-imidazole-5-carboxylic acid and 48 parts of thionyl chloride was refluxed for about 2 hours. After cooling there was added anhydrous 1,1'-oxybisethane. The formed precipitate was filtered off and washed on the filter with anhydrous 1,1'-oxybisethane. The filtercake was added to 20 parts of 1-propanol and the mixture was refluxed for 2 hours. The reaction mixture was evaporated in vacuo. The residue was divided between 105 parts of anhydrous 1,1'-oxybisethane and 20 parts of a sodium hydroxide solution 10N. The organic solution was washed with water, dried over magnesium sulfate, filtered and a saturated solution of gaseous hydrogen chloride in 2-propanol was added to the filtrate. The precipitated oily hydrochloride solidified on scratching; the solid was filtered off and dissolved in a small volume of 1-propanol. Anhydrous 1,1'-oxybisethane was added to this solution and after cooling, the formed precipitate was filtered off. It was recrystallized by dissolving in 2-propanol, previously saturated with gaseous hydrogen chloride and addition of anhydrous 1,1'-oxybisethane to the solution. After cooling, the formed precipitate was filtered off and dried in vacuo at 40° C., yielding 1.5 parts of propyl 1-(1-phenylethyl)-1H-imidazole-5-carboxylate; mp. 156°–157° C. (compound 1.116).

Example 16

To a solution of 12.2 parts of ethyl 1-(1-phenylethyl)-1H-imidazole-5-carboxylate in 160 parts of 2-propanone were added 5 parts of a nitric acid solution 65%. The product solidifies on scratching, yielding 14 parts of ethyl 1-(1-phenylethyl)-1H-imidazole-5-carboxylate mononitrate; mp. 138°–139° C. (compound 1.146).

Example 17

A mixture of 1 part of 1-[1-(2-chlorophenyl)butyl]-1H-imidazole-5-carboxylic acid, 80 parts of methanol and 35.9 parts of a potassium methoxide solution 0.1N was stirred for 1 hour at reflux temperature. The reaction mixture was evaporated and the residue was dried in a dry pistol at 70° C., yielding 0.34 parts (26.7%) of potassium 1-[1-(2-chlorophenyl)butyl]-1H-imidazole-5-carboxylate dihydrate; mp. 70.7° C. (compound 2.14).

Example 18

To a stirred solution of 7 parts of R-(+) ethyl 1-(1-phenylethyl)-1H-imidazole-5-carboxylate in 19.5 parts of iodomethane were added 21.3 parts of dichloromethane and the whole was stirred for 24 hours at room temperature. The reaction mixture was evaporated and the residue was crystallized from 2-propanol. The product was filtered off and washed with petroleum ether, yielding 7.03 parts of 5-ethoxycarbonyl-3-methyl-1-(1-phenylethyl)-1H-imidazolium iodide; mp. 159.5° C.; $[\alpha]_D = -62.79°$ (10% water).

Example 19

To a stirred and cooled (0° C.) solution of 5.9 parts of methyl 1-[1-(2-chlorophenyl)butyl]-1H-imidazole-5-carboxylate in 130 parts of dichloromethane are added 3.4 parts of 3-chlorobenzenecarboperoxoic acid. After stirring for 24 hours at room temperature, the reaction mixture is washed with 100 parts of a solution of sodium hydrogen carbonate in water (0.03M) and water, dried, filtered and evaporated (<30° C.). The residue is purified by column chromatography over silica gel using a mixture of trichloromethane and methanol, saturated with ammonia (95:5 by volume) as eluent. The pure fractions are collected and the eluent is evaporated. The residue is crystallized from hexane. The product is filtered off and dried, yielding methyl 1-[1-(2-chlorophenyl)butyl]-1H-imidazole-5-carboxylate, $N^3$-oxide (compound 4.02)

All other compounds listed in tables 1 and 4 can be obtained by analogous methods of preparation.

We claim:

1. A 1-methyl-1H-imidazole-5-carboxylic acid derivative of formula

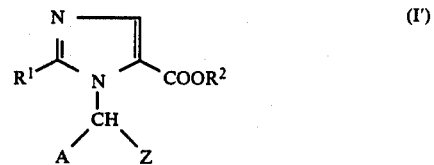

or a stereochemically isomeric form thereof, or a salt thereof, or a quaternised form thereof, or a N-oxide thereof, wherein $R^1$ is hydrogen or mercapto;

$R^2$ is aryl$C_1$-$C_5$alkyl or $C_3$-$C_7$cycloalkyl; wherein aryl is phenyl optionally substituted with one to three substituents independently selected from $C_1$-$C_5$alkyl, $C_1$-$C_5$alkyloxy and halo;

A is $C_3$-$C_7$cycloalkyl optionally substituted with one or two $C_1$-$C_5$alkyl radicals; $C_3$-$C_7$alkyl; $C_1$-$C_7$alkyl substituted with $C_1$-$C_7$alkyloxy or with an Ar radical; or $C_1$-$C_7$alkyl substituted with both a $C_1$-$C_7$alkyloxy and an Ar radical; or a radical selected from pyridinyl, pyrimidinyl, naphthalenyl, furanyl and thienyl, each unsubstituted or substituted with one or two radicals independently selected from $C_1$-$C_5$alkyl, $C_1$-$C_5$alkyloxy, halo, nitro, amino, mono- and di$C_1$-$C_5$alkylamino, —NH—CO—G, cyano, trifluoromethyl or difluoromethoxy; provided that when A is n-propyl then Z is other than phenyl;

said radical Ar being phenyl, pyridinyl, pyrimidinyl, naphthalenyl, furanyl or thienyl, each unsubstituted or substituted with one or two and in case Ar is phenyl also with three substituents selected from $C_1$-$C_5$alkyl, $C_1$-$C_5$alkyloxy, halo, nitro, amino, mono- and di$C_1$-$C_5$alkylamino, —NH—CO—G, cyano, trifluoromethyl and difluoromethoxy;

Z is naphthalenyl, thienyl, furanyl, pyrimidinyl, phenyl or pyridinyl, each unsubstituted or substituted with one or two substituents and in case Z is phenyl also with three substituents independently selected from $C_1$-$C_5$alkyl, $C_1$-$C_5$alkyloxy, halo, cyano, nitro, amino, mono- and di$C_1$-$C_5$alkylamino, —NH—CO—G, trifluoromethyl and difluoromethoxy; and G is $C_1$-$C_6$alkyl.

2. A compound according to claim 1 wherein wherein A is $C_3$-$C_7$cycloalkyl optionally substituted with one or two $C_1$-$C_5$alkyl radicals; branched $C_3$-$C_7$alkyl; $C_1$-$C_7$alkyl substituted with $C_1$-$C_7$alkyloxy or with an Ar radical; or $C_1$-$C_7$alkyl substituted with both a $C_1$-$C_7$alkyloxy and an Ar radical; or a radical selected from pyridinyl, pyrimidinyl, naphthalenyl, furanyl and thienyl, each unsubstituted or substituted with one or two radicals independently selected from $C_1$-$C_5$alkyl, $C_1$-$C_5$alkyloxy, halo, nitro, amino, mono- and di$C_1$-$C_5$alkylamino, —NH—CO—G, cyano, trifluoromethyl or difluoromethoxy.

3. A compound according to claim 2 wherein A is branched $C_3$-$C_7$alkyl, pyridinyl, naphthalenyl or $C_3$-$C_7$cycloalkyl optionally substituted with $C_1$-$C_5$alkyl and Z is pyridinyl, phenyl or phenyl substituted with $C_1$-$C_5$alkyloxy, $C_1$-$C_5$alkyl or halo.

4. A compound according to claim 3 wherein A is branched $C_3$-$C_5$alkyl, 2-pyridinyl, 3-pyridinyl or 4-pyridinyl and Z is phenyl or phenyl substituted with methoxy, methyl or chloro.

5. A herbicial composition, comprising one or more inert carriers and, if desired, other adjuvants, and as an active ingredient a herbicidally-effective amount of a 1-methyl-1H-imidazole-5-carboxylic acid derivative of formula

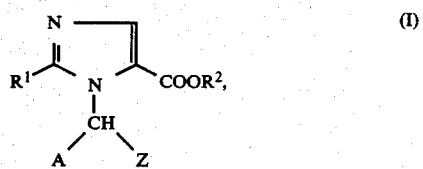

or a stereochemically isomeric form thereof, or a salt thereof, or a quaternised form thereof, or a N-oxide thereof, wherein $R^1$ is hydrogen or mercapto;

$R^2$ is hydrogen, aryl$C_1$–$C_5$alkyl or $C_3$–$C_7$cycloalkyl; wherein aryl is phenyl optionally substituted with one to three substituents independently selected from $C_a$–$C_5$alkyl, $C_1$–$C_5$alkyloxy and halo;

A is hydrogen; $C_3$–$C_7$cycloalkyl optionally substituted with one or two $C_1$–$C_5$alkyl radicals; $C_1$–$C_7$alkyl optionally substituted with $C_1$–$C_7$alkyloxy or with an Ar radical; or $C_1$–$C_7$alkyl substituted with both a $C_1$–$C_7$alkyloxy and an Ar radical; or a radical selected from pyridinyl, pyrimidinyl, naphthalenyl, furanyl and thienyl, each unsubstituted or substituted with one or two radicals independently selected from $C_1$–$C_5$alkyl, $C_1$–$C_5$alkyloxy, halo, nitro, amino, mono- and di$C_1$–$C_5$alkylamino, —NH—CO—G, cyano, trifluoromethyl or difluoromethoxy;

said radical Ar being phenyl, pyridinyl, pyrimidinyl, naphthalenyl, furanyl or thienyl, each unsubstituted or substituted with one or two and in case Ar is phenyl also with three substituents selected from $C_1$–$C_5$alkyl, $C_1$–$C_5$alkyloxy, halo, nitro, amino, mono- and di$C_1$–$C_5$alkylamino, —NH—CO—G, cyano, trifluoromethyl and difluoromethoxy;

Z is naphthalenyl, thienyl, furanyl, pyrimidinyl, phenyl or pyridinyl, each unsubstituted or substituted with one or two substituents and in case Z is phenyl also with three substituents independently selected from $C_1$–$C_5$alkyl, $C_1$–$C_5$alkyloxy, halo, cyano, nitro, amino, mono- and di$C_1$–$C_5$alkylamino, —NH—CO—G, trifluoromethyl and difluoromethoxy; and G is $C_1$–$C_6$alkyl.

6. A composition according to claim 5 wherein A is $C_3$–$C_7$cycloalkyl optionally substituted with one or two $C_1$–$C_5$alkyl radicals; $C_3$–$C_7$alkyl; $C_1$–$C_7$alkyl substituted with $C_1$–$C_7$alkyloxy or with an Ar radical; or $C_1$–$C_7$alkyl substituted with both a $C_1$–$C_7$alkyloxy and an Ar radical; or a radical selected from pyridinyl, pyrimidinyl, naphthalenyl, furanyl and thienyl, each unsubstituted or substituted with one or two radicals independently selected from $C_1$–$C_5$alkyl, $C_1$–$C_5$alkyloxy, halo, nitro, amino, mono- and di$C_1$–$C_5$alkylamino, —NH—CO—G, cyano, trifluoromethyl or difluoromethoxy; provided that when A is n-propyl then Z is other than phenyl.

7. A composition according to claim 6, wherein $R^2$ is hydrogen, A is $C_1$–$C_7$alkyl, naphthalenyl, pyridinyl or $C_3$–$C_7$-cycloalkyl optionally substituted with $C_1$–$C_5$alkyl and Z is pyridinyl, phenyl or phenyl substituted with $C_1$–$C_5$alkyloxy, $C_1$–$C_5$alkyl or halo.

8. A composition according to claim 7, wherein $R^2$ is hydrogen, A is $C_3$–$C_5$alkyl, 2-pyridinyl, 3-pyridinyl or 4-pyridinyl and Z is phenyl or phenyl substituted by methoxy, methyl or chloro.

9. A composition according to claim 5, wherein the active ingredient is 1-[1-(2-methoxyphenyl)butyl]-1H-imidazole-5-carboxylic acid, 1-[1-(2-chlorophenyl)butyl]-1H-imidazole-5-carboxylic acid, 1-[1-(2-methylphenyl)butyl]-1H-imidazole-5-carboxylic acid, 1-[1-(3-chlorophenyl)butyl]-1H-imidazole-5-carboxylic acid, or 1-[1-(2-pyridinyl)phenylmethyl]-1H-imidazole-5-carboxylic acid.

10. A composition according to claim 5, wherein $R^2$ is hydrogen or a base addition salt thereof.

11. A composition according to claim 5, wherein the active ingredient is

1-[1-(2-methoxyphenyl)butyl]-1H-imidazole-5-carboxylic acid,

1-[1-(2-chlorophenyl)butyl]-1H-imidazole-5-carboxylic acid,

1-[1-(2-methylphenyl)butyl]-1H-imidazole-5-carboxylic acid,

1-[1-(3-chlorophenyl)butyl]-1H-imidazole-5-carboxylic acid, or

1-[1-(2-pyridinyl)phenylmethyl]-1H-imidazole-5-carboxylic acid or a base addition salt thereof.

12. A method for controlling weeds, which method comprises applying to said weeds or to the locus thereof of a herbicidally effective amount of a 1-methyl-1H-imidazole-5-carboxylic acid derivative of formula

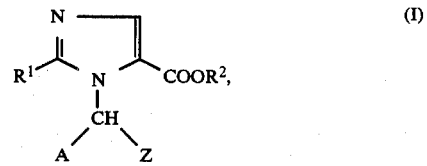

or a stereochemically isomeric form thereof, or a salt thereof, or a quaternised form thereof, or a N-oxide thereof, wherein $R^1$ is hydrogen or mercapto;

$R^2$ is hydrogen, $C_1$–$C_7$alkyl, $C_3$–$C_7$alkenyl, $C_3$–$C_7$alkynyl, $C_1$–$C_7$alkyloxy$C_1$–$C_7$alkyl, aryl$C_1$–$C_5$alkyl or $C_3$–$C_7$cycloalkyl; wherein aryl is phenyl optionally substituted with one to three substituents independently selected from $C_1$–$C_5$alkyl, $C_1$–$C_5$alkyloxy and halo;

A is hydrogen; $C_3$–$C_7$cycloalkyl optionally substituted with one or two $C_1$–$C_5$alkyl radicals; $C_1$–$C_7$alkyl optionally substituted with $C_1$–$C_7$alkyloxy or with an Ar radical; or $C_1$–$C_7$alkyl substituted with both a $C_1$–$C_7$alkyloxy and an Ar radical; or a radical selected from pyridinyl, pyrimidinyl, naphthalenyl, furanyl and thienyl, each unsubstituted or substituted with one or two radicals independently selected from $C_1$–$C_5$alkyl, $C_1$–$C_5$alkyloxy, halo, nitro, amino, mono- and di$C_1$–$C_5$alkylamino, —NH—CO—G, cyano, trifluoromethyl or difluoromethoxy;

said radical Ar being phenyl, pyridinyl, pyrimidinyl, naphthalenyl, furanyl or thienyl, each unsubstituted or substituted with one or two and in case Ar is phenyl also with three substituents selected from $C_1$–$C_5$alkyl, $C_1$–$C_5$alkyloxy, halo, nitro, amino, mono- and diC$_1$-C$_5$alkylamino, —NH—CO—G, cyano, trifluoromethyl and difluoromethoxy;

Z is naphthalenyl, thienyl, furanyl, pyrimidinyl, phenyl or pyridinyl, each unsubstituted or substituted with one or two substituents and in case Z is phenyl also with three substituents independently selected from C$_1$-C$_5$alkyl, C$_1$-C$_5$alkyloxy, halo, cyano, nitro, amino, mono- and diC$_1$-C$_5$alkylamino, —NH—CO—G, trifluoromethyl and difluoromethoxy; and G is C$_1$-C$_6$alkyl.

13. A method according to claim 12 for selectively controlling weeds in crops of useful plants.

14. A method according to claim 13 wherein the crop is rice.

15. A method according to claim 13 wherein the crop is maize.

16. A method according to claim 14 wherein the rice plants are transplanted rice plantlets.

17. A method according to claim 14 wherein 0.01 to 5.0 kg of active ingredient per hectare are applied to areas where rice crops are grown.

18. A method according to claim 17, wherein 0.05 to 1.0 kg of the active ingredient is applied per hectare after transplanting of the rice plantlets.

19. A method according to claim 12, wherein A is C$_3$-C$_7$cycloalkyl optionally substituted with one or two C$_1$-C$_5$alkyl radicals; C$_3$-C$_7$alkyl; C$_1$-C$_7$alkyl substituted with C$_1$-C$_7$alkyloxy or with an Ar radical; or C$_1$-C$_7$alkyl substituted with both a C$_1$-C$_7$alkyloxy and an Ar radical; or a radical selected from pyridinyl, pyrimidinyl, naphthalenyl, furanyl and thienyl, each unsubstituted or substituted with one or two radicals independently selected from C$_1$-C$_5$alkyl, C$_1$-C$_5$alkyloxy, halo, nitro, amino, mono- and diC$_1$-C$_5$alkylamino, —NH—CO—G, cyano, trifluoromethyl or difluoromethoxy; provided that when A is n-propyl then Z is other than phenyl.

20. A method according to claim 12, wherein R$^2$ is hydrogen or C$_1$-C$_7$alkyl, A is C$_1$-C$_7$-alkyl, naphthalenyl, pyridinyl or C$_3$-C$_7$cycloalkyl optionally substituted with C$_1$-C$_5$-alkyl and Z is pyridinyl, phenyl or phenyl substituted with C$_1$-C$_5$alkyloxy, C$_1$-C$_5$alkyl or halo.

21. A method according to claim 20, wherein R$^2$ is hydrogen, methyl or ethyl, A is C$_3$-C$_5$alkyl, 2-pyridinyl, 3-pyridinyl or 4-pyridinyl and Z is phenyl or phenyl substituted with methoxy, methyl or chloro.

22. A method according to claim 12, wherein the active ingredient is methyl 1-[1-(2-methoxyphenyl)butyl]-1H-imidazole-5-carboxylate, methyl 1-[1-(2-chlorophenyl)butyl]-1H-imidazole-5-carboxylate, methyl 1-[1-(2-methylphenyl)butyl]-1H-imidazole-5-carboxylate, methyl 1-[1-(3-chlorophenyl)butyl]-1H-imidazole-5-carboxylate, methyl 1-[1-(2-pyridinyl)phenylmethyl]-1H-imidazole-5-carboxylate, 1-[1-(2-methoxyphenyl)butyl]-1H-imidazole-5-carboxylic acid, 1-[1-(2-chlorophenyl)butyl]-1H-imidazole-5-carboxylic acid, 1-[1-(2-methylphenyl)butyl]-1H-imidazole-5-carboxylic acid, 1-[1-(3-chlorophenyl)butyl]-1H-imidazole-5-carboxylic acid, or 1-[1-(2-pyridinyl)phenylmethyl]-1H-imidazole-5-carboxylic acid.

23. A method according to claim 12, wherein 0.01 to 5.0 kg of active ingredient per hectare are applied to control said weeds.

24. A method according to claim 12, wherein R$^2$ is hydrogen or a base addition salt thereof.

25. A method according to claim 12, wherein the active ingredient is

1-[1-(2-methoxyphenyl)butyl]-1H-imidazole-5-carboxylic acid,

1-[1-(2-chlorophenyl)butyl]-1H-imidazole-5-carboxylic acid,

1-[1-(2-methylphenyl)butyl]-1H-imidazole-5-carboxylic acid,

1-[1-(3-chlorophenyl)butyl]-1H-imidazole-5-carboxylic acid, or

1-[1-(2-pyridinyl)phenylmethyl]-1H-imidazole-5-carboxylic acid or a base addition salt thereof.

* * * * *